US009913844B2

(12) United States Patent
Caponigro et al.

(10) Patent No.: US 9,913,844 B2
(45) Date of Patent: Mar. 13, 2018

(54) COMBINATION THERAPY

(71) Applicant: Novartis AG, Basel (CH)

(72) Inventors: Giordano Caponigro, Cambridge, MA (US); Darrin Stuart, Emeryville, CA (US); Laure De Parseval, Basel (CH)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/777,873

(22) PCT Filed: Mar. 19, 2014

(86) PCT No.: PCT/IB2014/059975
§ 371 (c)(1),
(2) Date: Sep. 17, 2015

(87) PCT Pub. No.: WO2014/147573
PCT Pub. Date: Sep. 25, 2014

(65) Prior Publication Data
US 2016/0296520 A1  Oct. 13, 2016

Related U.S. Application Data

(60) Provisional application No. 61/804,056, filed on Mar. 21, 2013.

(51) Int. Cl.
A61K 31/506 (2006.01)
A61K 45/06 (2006.01)
A61K 31/4184 (2006.01)
A61K 31/4439 (2006.01)
A61K 31/4745 (2006.01)
A61K 31/496 (2006.01)
A61K 31/519 (2006.01)
A61K 31/53 (2006.01)
A61K 31/5377 (2006.01)
A61K 9/00 (2006.01)
A61K 9/20 (2006.01)
A61K 9/48 (2006.01)
C12Q 1/68 (2018.01)

(52) U.S. Cl.
CPC .......... A61K 31/506 (2013.01); A61K 9/0053 (2013.01); A61K 9/20 (2013.01); A61K 9/48 (2013.01); A61K 31/4184 (2013.01); A61K 31/4439 (2013.01); A61K 31/4745 (2013.01); A61K 31/496 (2013.01); A61K 31/519 (2013.01); A61K 31/53 (2013.01); A61K 31/5377 (2013.01); A61K 45/06 (2013.01); C12Q 1/6886 (2013.01); C12Q 2600/106 (2013.01); C12Q 2600/156 (2013.01)

(58) Field of Classification Search
CPC .............. A61K 31/306; A61K 31/4184; A61K 31/519; A61K 31/53; A61K 9/0053; A61K 9/48; A61K 9/20; C12Q 1/6886
See application file for complete search history.

(56) References Cited

U.S. PATENT DOCUMENTS

| 8,436,177 B2 * | 5/2013 | Stowasser ............ C07D 471/04 546/82 |
| 8,501,758 B2 | 8/2013 | Huang et al. |
| 8,563,549 B2 | 10/2013 | Burger et al. |
| 2009/0137804 A1 | 5/2009 | Ding et al. |

FOREIGN PATENT DOCUMENTS

| EP | 2 570 127 A1 | 3/2013 |
| WO | 2003/077914 A1 | 9/2003 |
| WO | 2006/053201 A2 | 5/2006 |
| WO | 2007/084786 A1 | 7/2007 |
| WO | 2009/143211 A2 | 11/2009 |
| WO | 2011/025927 A1 | 3/2011 |
| WO | 2011/046894 A1 | 4/2011 |
| WO | 2012/068468 A1 | 5/2012 |
| WO | 2012/095505 A1 | 7/2012 |
| WO | 2012/178038 A1 | 12/2012 |
| WO | 2013/043715 A1 | 3/2013 |
| WO | 2014/018725 A1 | 1/2014 |
| WO | 2014/025688 A1 | 2/2014 |

OTHER PUBLICATIONS

Flaherty et al. (Cancer 2010); 116(21); 4902-4913.*
Puzanov et al. vol. 5, Issue 2, Apr. 2011, pp. 116-123.*
Flaherty et al. (Nov. 2012) "Combined BRAF and MEK inhibition in melanoma with BRAF V600 mutations," New England Journal of Medicine. 367(18):1694-1703.
Giroux (Jan. 2013) "Overcoming acquired resistance to kinase inhibition: The cases of EGFR, ALK and BRAF," Bioorganic and Medicinal Chemistry Letters. 23(2):394-401.
Holash (Sep. 2012) "Preclinical strategies to help better identify responder populations in the clinic," Novartis Institutes for Biomedical Research. In; NorCal SOT Fall Symposium: New Frontiers in Oncology Drug Development. Sep. 27, 2012. San Francisco, California.
Huilllard et al. (May 2012) "Cooperative interactions of BRAFV600E kinase and CDKN2A locus deficiency in pediatric malignant astrocytoma as a basis for rational therapy," Proc. Natl. Acad. Sci. USA. 109(22):8710-8715.

(Continued)

Primary Examiner — Shirley V Gembeh
(74) Attorney, Agent, or Firm — Brian C. Trinque; Lathrop Gage LLP

(57) ABSTRACT

Reversing resistance to a B-Raf inhibitor for the treatment of a proliferative disease by obtaining a tumor sample from the patient and testing it for genetic alterations in a panel of genes comprising BRAF, CRAF, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16 and administering a drug combination therapy comprising the B-Raf inhibitor and a second inhibitor which overcomes resistance to the B-Raf inhibitor, which second inhibitor is selected based on genetic alterations discovered in the tumor sample.

3 Claims, 4 Drawing Sheets

(56) References Cited

OTHER PUBLICATIONS

International Melanoma Congress "2011 International Melanoma Congress," Pigment Cell and Melanoma Research. 24(5):990-1075, Abstract SMR-P91 on p. 1049.

McCain (Feb. 2013) "The MAPK (ERK) Pathway: Investigational Combinations for the Treatment of BRAF-Mutated Metastatic Melanoma," P&T. 38(2):96-108.

Metzner et al. (Jul. 2011) "Fibroblast growth factor receptors as therapeutic targets in human melanoma: synergism with BRAF inhibition," Journal of Investigative Dermatology. 131(1):2087-2095.

Smalley et al. (2009) "Integrating BRAF/MEK inhibitors into combination therapy for melanoma," British Journal of Cancer. 100(3):431-435.

Su et al. (Feb. 2012) "Resistance to selective BRAF inhibition can be mediated by modest upstream pathway activation," Cancer Research. 72(4):969-978.

Sullivan et al. (Jan. 2013) "Resistance to BRAF-targeted therapy in melanoma," European Journal of Cancer. 49 (6):1297-1304.

Vergani et al. (Dec. 2011) "Identification of MET and SRC Activation in Melanoma Cell Lines Showing Primary Resistance to PLX4032," Neoplasia. 13(12):1132-1142.

Wolf et al. (Mar. 2012) "Abstract LB-122: A phase I dose escalation study of NVP-BGJ398, a selective pan FGFR inhibitor in genetically preselected advanced solid tumors," Proceedings of the 103rd Annual Meeting of the American Association for Cancer Research. Mar 31-Apr. 4, 2012. Chicago, Illinois. Accessible on the Internet at URL: http://cancerres.aacrjournals.org/content/72/8_Supplement/LB-122.short. [Last Accessed Jan. 20, 2016].

International Preliminary Report on Patentability corresponding to International Patent Application No. PCT/IB2014/059975, dated Sep. 22, 2015.

International Search Report with Written Opinion corresponding to International Patent Application No. PCT/IB2014/059975, dated Oct. 1, 2014.

* cited by examiner

COMBINATION THERAPY

RELATED APPLICATIONS

This application is a 371 filing of Patent Cooperation Treaty Application No. PCT/IB2014/055975, filed Mar. 19, 2014, which claims priority to U.S. Patent Application No. 61/804,056, filed Mar. 21, 2013, the contents of which are incorporated herein by reference in their entirety.

SUMMARY

The present invention relates to the use of a B-Raf inhibitor in combination with a second inhibitor for the treatment of a patient suffering from a proliferative disease characterized by a mutation in B-Raf, wherein the second inhibitor is selected based on genetic alterations identified in a tumor sample.

BACKGROUND

Important advances have been made in the understanding of the molecular changes associated with the development of melanoma. Oncogenic mutations of B-RAF, a serine-threonine protein kinase in the RAF/MEK/ERK pathway, are particularly common in melanoma, with 40 to 60% of melanoma carrying an activating mutation in the B-Raf gene. The substitution of glutamic acid for valine at amino acid 600 (V600E mutation) represents more than 95% of the reported B-Raf mutations. This mutation constitutively activates B-Raf and downstream signal transduction in the RAF/MEK/ERK pathway, which signals for cancer cell proliferation and survival. In addition to melanoma, such mutations of B-Raf are known to occur in other proliferative diseases, for example, colorectal cancer, thyroid cancer, particularly papillary thyroid cancer, astrocytomas, pancreatic cancer, and neurofibromatosis. Although dramatic results are known to occur when such diseases are treated with a B-Raf inhibitor, the development of resistance to treatment with the B-Raf inhibitor is typical, often occurring within a fairly short period of time.

There are multiple paths to resistance to treatment with a B-Raf inhibitor. The main mechanisms result in reactivation of the RAF/MEK/ERK signaling pathway in the presence of the B-Raf inhibitor. This reactivation can occur via increased activity of receptor tyrosine kinases (RTKs) via gene amplification, and over expression and/or ligand production, acquisition of mutations in the NRAS and MEK1 genes, bypass of BRAF via over-expression of kinases such as COT and RAF-1 (CRAF), expression of splice variants of the mutant BRAF allele, and increased expression of the mutant BRAF allele due to, e.g. gene amplification. In addition, activation of survival pathways such as the PIK3Cα signaling system that are distinct from the MAPK pathway, either via activation of RTKs such as PDGFR-β and IGF-1R or loss of the PTEN gene may also play a role in resistance. Other mechanisms, through c-MET and the FGFR family of RTKs, are potential mechanisms that may promote resistance to B-Raf inhibitors in multiple melanoma.

The findings described above highlight the importance of identifying mechanisms of resistance in real time, in order to initiate a rational combination therapy early on after relapse on B-Raf inhibitor treatment. Using a mechanism-based approach with the comparison of the genetic alterations present in a patient's tumor at the time of relapse versus pre-treatment, it should be possible to identify likely resistance mechanisms. This will help selecting the appropriate drug combination therapy for an individual patient in order to better circumvent resistance. The present invention relates to a mechanism-based combination treatment approach to expand and improve the therapeutic options for patients with BRAF-mutant advanced or metastatic melanoma that have very poor prognosis after the development of resistance to B-Raf inhibitors.

BRIEF DESCRIPTION

The present invention relates to treating a patient suffering from a proliferative disease characterized by a mutation in B-Raf with a B-Raf inhibitor wherein resistance to the B-Raf inhibitor is reduced by
(a) determining genetic alterations in a tumor sample taken from the patient,
(b) administering a drug combination therapy consisting of the B-Raf inhibitor and a second inhibitor to the patient, wherein the second inhibitor is selected based on the genetic alterations found in the tumor sample.

DETAILED DESCRIPTION

Figure 1:
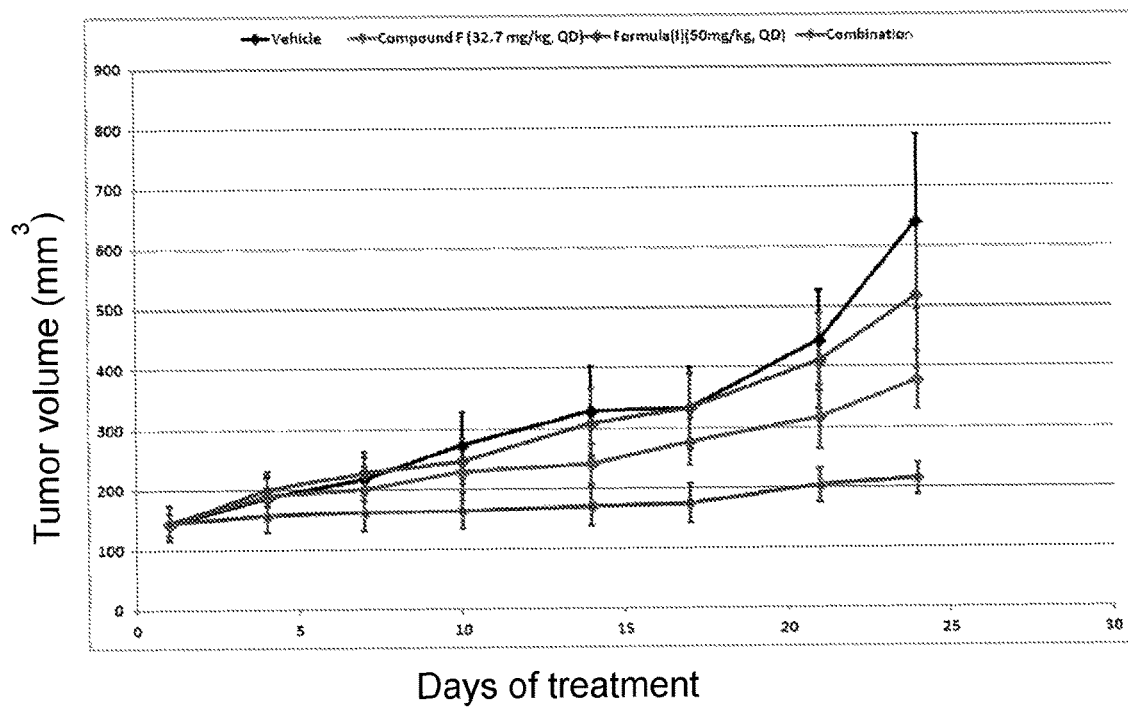
FIG. 1—shows the effect of the Compound of Formula (I) and Compound F as single agents and in combination on the growth of the HT-29 cell line model in vivo as described in Example 4.

The present invention relates to a method for treating a patient suffering from a proliferative disease characterized by a mutation in B-Raf, particularly a V600 mutation in B-Raf, which comprises:
(a) obtaining a tumor sample from the patient and testing for a genetic alteration in a panel of genes comprising BRAF, CRAF, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16.
(b) administering a drug combination therapy comprising a B-Raf inhibitor and a second inhibitor, which second inhibitor is selected based on genetic alterations discovered in the tumor sample.

In one embodiment, the proliferative disease is cancer. The term "cancer" is used herein to mean a broad spectrum of tumors, including all solid tumors and hematological malignancies. Examples of such tumors include but are not limited to benign or malignant tumors of the brain, lung (in particular small-cell lung cancer and non-small cell lung cancer), squamous cell, bladder, gastric, pancreatic, breast, head and neck, renal, kidney, ureter, ovarian, prostate, colorectal, esophageal, testicular, gynecological (e.g., uterine sarcomas, carcinoma of the fallopian tubes, endometrial, cervix, vagina or vulva), thyroid, pancreatic, bone, skin, melanoma, uterine, ovarian, rectal, anal, colon, testicular, Hodgkin's disease, esophageal, small intestine, endocrine system (e.g., thyroid, parathyroid, or adrenal glands), sarcomas of soft tissues, urethra, penis, leukemia, lymphomas, neoplasms of the central nervous system, sarcomas, myeloma, biliary, liver, neurofibromatosis, acute myelogenous leukemia (AML), myelodysplastic syndromes (MDS), and Kaposi's sarcoma.

In a further embodiment of the present invention, the proliferative disease is melanoma, lung cancer (including non-small cell lung cancer (NSCLC)), colorectal cancer (CRC), breast cancer, kidney cancer such as e.g., renal cell carcinoma (RCC), liver cancer, endometrial cancer, acute myelogenous leukemia (AML), myelodysplastic syndromes (MDS), thyroid cancer, particularly papillary thyroid cancer, pancreatic cancer, neurofibromatosis or hepatocellular carcinoma.

In a further embodiment of the present invention, the proliferative disease is a solid tumor. The term "solid tumor" especially means melanoma, breast cancer, ovarian cancer, colorectal cancer, and generally gastrointestinal tract, cervix cancer, lung cancer (including small-cell lung cancer and non-small cell lung cancer), head and neck cancer, bladder cancer, prostate cancer or Kaposi's sarcoma.

More particularly, the present invention relates to a method for treating a patient suffering from a proliferative disease characterized by a V600 mutation in B-Raf, for example a V600E mutation. Proliferative diseases frequently characterized by such a mutation include melanoma, colorectal cancer, thyroid cancer, particularly papillary thyroid cancer, astrocytomas, pancreatic cancer, and neurofibromatosis. The present invention especially relates to such a method wherein the proliferative disease is melanoma characterized by a V600 mutation in B-Raf, for example a V600E, V600K or V600G mutation.

B-Raf inhibitors and their use for treating proliferative diseases are known in the art. Vemurafenib (PLX4032) is a BRAF inhibitor which was approved by the FDA for the treatment of patients with melanoma whose tumors express BRAF V600E. Sorafenib and dabrafenib and CEP-32496 are additional known B-Raf inhibitors. The benzimidazolyl pyridyl ethers, disclosed in U.S. Pat. No. 7,482,367, which is here incorporate by reference in its entirety, are B-Raf inhibitors useful in the present combinations, particularly RAF265. The pyrrazole pyrimidines, which are disclosed in WO 2011/025927 and which is here incorporate by reference in its entirety, are another class of B-Raf inhibitors useful for the present combinations.

An appropriate second inhibitor to be combined with the B-Raf inhibitor is selected in accordance with Table 1 for treatment of the patient based on the genetic alterations found in the tumor sample. The genetic alterations can result from amplification of a gene, mutations in a gene or loss of the gene's activity.

TABLE 1

| Genetic Alterations | | | Drug to be given in combination with the B-Raf inhibitor |
|---|---|---|---|
| Amplification | Mutation | Loss | |
| BRAF | MAP2K1 | | Mek1/2 inhibitor |
| CRAF | MAP2K2 | | |
| EGFR | NRAS | | |
| | KRAS HRAS | | |
| CCND1 | CDK4 | P16 | CDK 4 inhibitor |
| CDK4 | | | |
| HER2 | PTEN | PTEN | PI3 Kinase |
| IGF-1R | PIK3CA | | inhibitor |
| cMET | | | c-Met receptor tyrosine kinase inhibitor |
| FGFR1 | | | FGFR kinase |
| FGFR2 | | | inhibitor |
| FGFR3 | | | |
| Or no alteration in any of the above identified genes | | | Mek1/2 inhibitor |

The information relating to the genes identified in Table 1, their sequences and associated proteins are known to those of skill in the art and are found in publically available databases, for example, those provided by National Center for Biotechnology Information, U.S. National Library of Medicine8600 Rockville Pike, Bethesda Md., 20894USA, such as GENE (URL: http://www.ncbi.nlm.nih.gov/gene) or Office of Biological and Environmental Research of the U.S. Department of Energy Office of Science, Human Genome Project Information (URL: http://genomics.energy.gov/).

The drug combination therapy involves administering each of the drugs in the combination therapy in an amount sufficient to provide an observable improvement over the baseline clinically observable signs and symptoms of the disorder treated with the combination. The drugs may be given separately (in a chronologically staggered manner, especially a sequence-specific manner) in such time intervals that they prefer, such that in the patient shows a (preferably synergistic) interaction (joint therapeutic effect), in particular wherein resistance to treatment with the B-Raf inhibitor is overcome or reduced in the patient.

The term "pharmaceutically effective amount" or "clinically effective amount" or "therapeutically effective amount" of a combination of therapeutic agents is an amount sufficient to provide an observable improvement over the baseline clinically observable signs and symptoms of the disorder treated with the combination.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "combination", "therapeutic combination" "combination therapy" or "pharmaceutical combination", as used herein, defines either a fixed combination in one dosage unit form or a kit of parts or instructions for the combined administration where the B-Raf inhibitor and the second inhibitor may be administered independently at the same time or separately within time intervals that allow that the combination partners show a cooperative, e.g., synergistic, effect.

The term "pharmaceutical composition" is defined herein to refer to a mixture or solution containing at least one therapeutic agent to be administered to a subject, e.g., a mammal or human, in order to prevent or treat a particular disease or condition affecting the mammal.

The term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

A "pharmaceutically acceptable salt", as used herein, unless otherwise indicated, includes salts of acidic and basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of the present invention are those that form non-toxic acid addition salts, i.e., salts containing pharmaceutically acceptable anions, such as the acetate, benzoate, bromide, chloride, citrate, fumarate, hydrobromide, hydrochloride, iodide, lactate, maleate, mandelate, nitrate, oxalate, salicylate, succinate, and tartrate salts. Unless otherwise specified, the therapeutic agents used in the inventive methods are administered in free form or as a pharmaceutically salt.

The term "a combined preparation" is defined herein to refer to especially a "kit of parts" in the sense that the combination partners (a) and (b) as defined above can be dosed independently or by use of different fixed combinations with distinguished amounts of the combination partners (a) and (b), i.e., simultaneously or at different time points. The parts of the kit of parts can then e.g., be administered simultaneously or chronologically staggered, that is at different time points and with equal or different time intervals for any part of the kit of parts. The ratio of the total amounts of the combination partner (a) to the combination partner (b) to be administered in the combined preparation can be varied, e.g., in order to cope with the needs of a patient sub-population to be treated or the needs of the single patient.

The term "co-administration" "combination therapy" or "combined administration" as used herein is defined to encompass the administration of the selected therapeutic agents to a single patient, and are intended to include treatment regimens in which the agents are not necessarily administered by the same route of administration or at the same time.

The term "treating" or "treatment" as used herein comprises a treatment relieving, reducing or alleviating at least one symptom in a subject or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

The term "subject" or "patient" as used herein refers particularly to a human, e.g., a human suffering from, at risk of suffering from, or potentially capable of suffering from the proliferative disease. However, it is not intended to exclude the treatment of mammals, e.g., dogs, cows, horses, pigs, sheep, goats, cats, mice, rabbits rats and transgenic non-human animals.

The term about" or "approximately" shall have the meaning of within 10%, more preferably within 5%, of a given value or range.

Thus, the present invention relates to a method for treating a patient suffering from a proliferative disease characterized by a mutation in B-Raf, particularly a V600 mutation in B-Raf, very particularly a melanoma characterized by a V600 mutation in B-Raf, which comprises:

(a) obtaining a tumor sample from the patient and testing for a genetic alteration in a gene selected from the group comprising BRAF, CRAF, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16.

(b) administering a drug combination therapy comprising a B-Raf inhibitor and a second inhibitor, which second inhibitor is selected based on genetic alterations discovered in the tumor sample in accordance with Table 1, particularly wherein, (i) the second inhibitor is a Mek 1/2 inhibitor when the tumor sample has a genetic alteration in BRAF, CRAF, MAP2K1, MAPK2, NRAS, KRAS HRAS or EGFR, or (ii) the second inhibitor is a CDK 4 inhibitor when the tumor sample has a genetic alteration in CCND1, CDK4 or P16, or (iii) the second inhibitor is a PI3 Kinase inhibitor when the tumor sample has a genetic alteration in HER2, IGF-1R, PTEN or PIK3CA, or (iv) the second inhibitor is a c-Met receptor tyrosine kinase inhibitor when the tumor sample has a genetic alteration in cMET, (v) the second inhibitor is a FGFR kinase inhibitor when the tumor sample has a genetic alteration in FGFR1, FGFR2 or FGFR3.

Thus, the present invention further relates to a method for treating a patient suffering from a proliferative disease characterized by a mutation in B-Raf, particularly a V600 mutation in B-Raf, very particularly a melanoma characterized by a V600 mutation in B-Raf, which comprises:

(a) obtaining a tumor sample from the patient and detecting a genetic alteration in a gene selected from the group comprising BRAF, CRAF, MAP2K1, MAPK2, NRAS, KRAS HRAS or EGFR.

(b) administering a drug combination therapy to the patient comprising the B-Raf inhibitor and a second inhibitor which is a Mek 1/2 inhibitor.

The present invention also relates to a method for treating a patient suffering from a proliferative disease characterized by a mutation in B-Raf, particularly a V600 mutation in B-Raf, very particularly a melanoma characterized by a V600 mutation in B-Raf, which comprises:

(b) obtaining a tumor sample from the patient and detecting a genetic alteration in a gene selected from the group comprising CCND1, CDK4 or P16.

(d) administering a drug combination therapy to the patient comprising the B-Raf inhibitor and a second inhibitor which is a CDK 4 inhibitor.

The present invention relates to a method for treating a patient suffering from a proliferative disease characterized by a mutation in B-Raf, particularly a V600 mutation in B-Raf, very particularly a melanoma characterized by a V600 mutation in B-Raf, which comprises:
(a) obtaining a tumor sample from the patient after disease progression and detecting a genetic alteration in a gene selected from the group comprising HER2, IGF-1R, PTEN or PIK3CA,
(b) administering a drug combination therapy to the patient comprising the B-Raf inhibitor and a second inhibitor which is a PI3 Kinase inhibitor.

The present invention relates to a method for treating a patient suffering from a proliferative disease characterized by a mutation in B-Raf, particularly a V600 mutation in B-Raf, very particularly a melanoma characterized by a V600 mutation in B-Raf, which comprises:
(a) obtaining a tumor sample and detecting a genetic alteration in a gene selected from the group comprising cMET,
(b) administering a drug combination therapy to the patient comprising the B-Raf inhibitor and a second inhibitor which is a c-Met receptor tyrosine kinase inhibitor.

The present invention relates to a method for treating a patient suffering from a proliferative disease characterized by a mutation in B-Raf, particularly a V600 mutation in B-Raf, very particularly a melanoma characterized by a V600 mutation in B-Raf, which comprises:
(a) obtaining a tumor sample from the patient and detecting a genetic alteration in a gene selected from the group comprising FGFR1, FGFR2 or FGFR3
(b) administering a drug combination therapy to the patient comprising the B-Raf inhibitor and a second inhibitor which is a FGFR kinase inhibitor.

In an important embodiment of the present invention, the patient has been treated previously with B-Raf inhibitor monotherapy. Particularly, the patient is treated with B-Raf inhibitor monotherapy until disease progression followed by a drug combination therapy determined in accordance with Table 1.

In a preferred embodiment, the B-Raf inhibitor is administered continuously as a monotherapy until disease progression or initiation of the drug combination therapy and the continuous administration is continued during treatment with the drug combination therapy.

In another embodiment, the B-Raf inhibitor is administered on an intermittent dosing schedule, which means that that the B-Raf inhibitor is administered for a period of time followed by a period of time wherein treatment with the B-Raf inhibitor is withheld. For example, the Raf inhibitor is administered daily for a period of 3 or 4 weeks followed by a period of 1 or 2 weeks without treatment and the cycle is repeated.

Disease progression is evaluated by appropriate clinical criteria, such as the RECIST criteria. RECIST (Response Evaluation Criteria In Solid Tumors) is a set of published rules that define when cancer patients improve ("respond"), stay the same ("stable") or worsen ("progression") during treatments. The original criteria were published in February 2000 by an international collaboration including the European Organization for Research and Treatment of Cancer (EORTC), National Cancer Institute (NCI) of the United States and the National Cancer Institute of Canada Clinical Trials Group. RECIST 1.1, published in January 2009, is an update to the original criteria. See, Eur. J. Cancer, 45, (2009) 228-247.

A mechanism for disease progression is determined by comparison of the genetic alterations present in a patient's tumor at the time of relapse, for example, versus pre-treatment. The genetic alterations can result from amplification of a gene, mutations in a gene or loss of the gene's activity. The genetic alterations are determined by methods known in the art, typically by known sequencing methods. In a preferred embodiment, genes selected from the group consisting of B-Raf, C-Raf, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16 in tumor samples taken at the time of relapse versus pre-treatment are compared.

Thus, the present invention also relates to testing a tumor sample obtained from a patient suffering from a proliferative disease characterized by a mutation in B-Raf, particularly a V600 mutation in B-Raf, very particularly a melanoma characterized by a V600 mutation in B-Raf, for genetic alterations in a panel of genes comprising B-Raf, C-Raf, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16 in order to determine a mechanism of disease progression after treatment with a B-Raf inhibitor.

The present invention also relates to a diagnostic method for selecting a second inhibitor to be combined with a B-Raf inhibitor wherein a tumor sample is tested for genetic alterations one of more genes selected from B-Raf, C-Raf, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16. The second inhibitor is selected in accordance with Table 1. Preferably, the second inhibitor is selected to overcome resistance to treatment with the B-Raf inhibitor.

The present invention also relates a gene chip useful for detecting for genetic alterations in one of more genes selected from B-Raf, C-Raf, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16, or which comprises all or a subset of the aforementioned genes. The gene chip is useful for determining a mechanism of resistance to treatment with a B-Raf inhibitor and for selecting a second inhibitor to be used in drug combination therapy which overcomes that resistance.

A particular embodiment of the present invention is a method for treating a patient suffering from a proliferative disease characterized by a mutation in B-Raf, particularly a V600 mutation in B-Raf, very particularly a melanoma characterized by a V600 mutation in B-Raf, which comprises:
(a) administering a therapeutically effective amount of a B-Raf inhibitor to the patient until the patient exhibits disease progression,
(b) obtaining a tumor sample from the patient after disease progression and testing for a genetic alteration in one or more genes selected from the group consisting of BRAF, CRAF, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16, and
(c) administering a drug combination therapy comprising the B-Raf inhibitor and a second inhibitor, which second inhibitor is selected based on genetic alterations found in the tumor sample, wherein,
    (i) the second inhibitor is a Mek 1/2 inhibitor when the genetic alteration is in BRAF, CRAF, MAP2K1, MAPK2, NRAS, KRAS HRAS or EGFR, or
    (ii) the second inhibitor is a CDK 4 inhibitor when the genetic alteration is in CCND1, CDK4 or P16, or
    (iii) the second inhibitor is a PI3 Kinase inhibitor when the genetic alteration is in HER2, IGF-1R, PTEN or PIK3CA, or (iv) the second inhibitor is a c-Met receptor tyrosine kinase inhibitor when the genetic alteration is in cMET, or
(v) the second inhibitor is a FGFR kinase inhibitor when the genetic alteration is in FGFR1, FGFR2 or FGFR3.

A preferred B-Raf inhibitor useful in the present invention is a Compound of Formula (I)

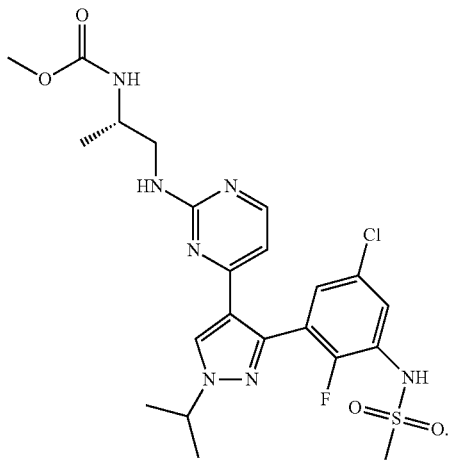

The Compound of formula (I) and its utility as a B-Raf inhibitor are disclosed in WO 2011/025927.

Thus, the present invention more particularly relates to a method for treating a patient suffering from a proliferative disease characterized by a mutation in B-Raf, particularly a V600 mutation in B-Raf, very particularly a melanoma characterized by a V600 mutation in B-Raf, which comprises:
(a) obtaining a tumor sample from the patient and testing for a genetic alteration in one or more genes selected from the group consisting of BRAF, CRAF, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16, and
(b) administering a drug combination therapy comprising a B-Raf inhibitor of the formula (I)

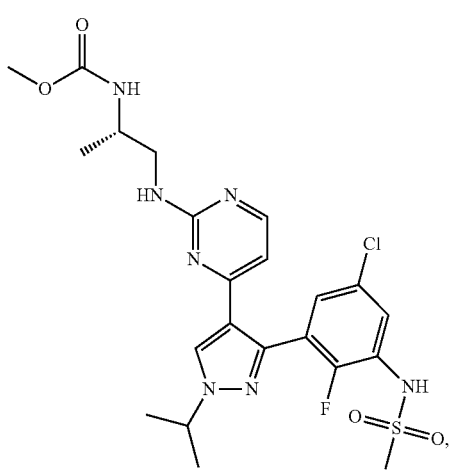

or a pharmaceutically acceptable salt thereof, and a second inhibitor, which second inhibitor is selected based on genetic alterations discovered in the tumor sample in accordance with Table 1, particularly wherein,
(i) the second inhibitor is a Mek 1/2 inhibitor when the tumor sample has a genetic alteration in BRAF, CRAF, MAP2K1, MAPK2, NRAS, KRAS HRAS or EGFR, or when no genetic alteration is found in step (b), or
(ii) the second inhibitor is a CDK 4 inhibitor when the tumor sample has a genetic alteration in CCND1, CDK4 or P16, or
(iii) the second inhibitor is a PI3 Kinase inhibitor when the tumor sample has a genetic alteration in HER2, IGF-1R, PTEN or PIK3CA, or
(iv) the second inhibitor is a c-Met receptor tyrosine kinase inhibitor when the tumor sample has a genetic alteration in cMET, or
(v) the second inhibitor is a FGFR kinase inhibitor when the tumor sample has a genetic alteration in FGFR1, FGFR2 or FGFR3.

A more specific embodiment of the present invention includes providing monotherapy with the B-Raf inhibitor of Formula (I) prior to the drug combination therapy. Thus, the present invention further relates to a method for treating a patient suffering from a proliferative disease characterized by a mutation in B-Raf, particularly a V600 mutation in B-Raf, very particularly a melanoma characterized by a V600 mutation in B-Raf, which comprises:
(a) administering to the patient a therapeutically effective amount of a B-Raf inhibitor of the formula (I)

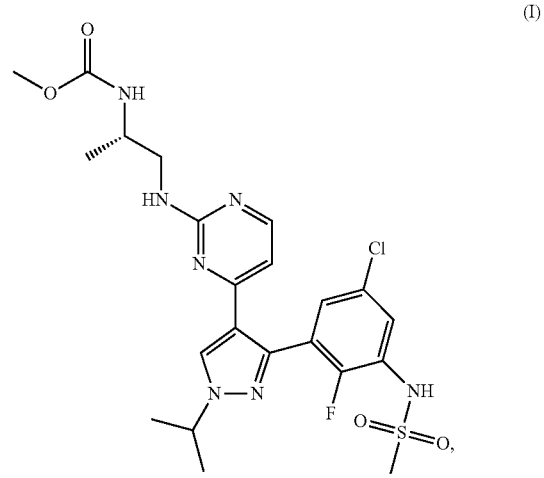 [SMILES: COC(=O)N[C@@H](C)CNc1nccc(-c2cn(C(C)C)nc2-c2cc(Cl)cc(NS(C)(=O)=O)c2F)n1]

or a pharmaceutically acceptable salt thereof, until the patient exhibits disease progression,
(b) obtaining a tumor sample from the patient after disease progression and testing for a genetic alteration in one or more genes selected from the group consisting of B-Raf, C-Raf, CCND1, CDK4, HER2, IGF-1R, cMET, FGFR1, FGFR2, FGFR3 EGFR, MAP2K1, MAP2K2, NRAS, KRAS HRAS, PTEN, PIK3CA, and P16,
(c) administering a drug combination therapy comprising the B-Raf inhibitor and a second inhibitor, which second inhibitor is selected based on the genetic alteration discovered in the tumor sample in accordance with Table 1, particularly wherein,
(i) the second inhibitor is a Mek 1/2 inhibitor when the mechanism of disease progression is characterized by a genetic alteration in BRAF, CRAF, MAP2K1, MAPK2, NRAS, KRAS HRAS or EGFR, or when no genetic alteration is found in step (b), or (ii) the second inhibitor is a CDK 4 inhibitor when the mechanism of disease progression is characterized by a genetic alteration in CCND1, CDK4 or P16, or (iii) the second inhibitor is a PI3 Kinase inhibitor when the mechanism of disease progression is characterized by a genetic alteration in HER2, IGF-1R, PTEN or PIK3CA, or (iv) the second inhibitor is a c-Met receptor tyrosine kinase inhibitor when the mechanism of disease progression is characterized by a genetic alteration in cMET, or (v) the second inhibitor is a FGFR kinase inhibitor when the mechanism of disease progression is characterized by a genetic alteration in FGFR1, FGFR2 or FGFR3.

The Compound of Formula (I) may be administered continuously or on an intermittent dosing schedule in steps (a) and (c). It is preferably administered continuously.

In each of the aforementioned methods, preferred embodiments especially include those wherein the proliferative disease is characterized by a V600 mutation in B-Raf, for example a V600E mutation. Proliferative diseases frequently characterized by such a mutation include melanoma, colorectal cancer, thyroid cancer, particularly papillary thyroid cancer, astrocytomas, pancreatic cancer, and neurofibromatosis. Preferably, the proliferative disease is melanoma or colorectal cancer characterized by a V600 mutation in B-Raf, for example a V600E, V600K or V600G mutation. The present invention especially relates to such a method wherein the proliferative disease is melanoma characterized by a V600 mutation in B-Raf, for example a V600E, V600K or V600G mutation.

Appropriate Mek 1/2 inhibitors for use in the present method are known in the art. Mek 1/2 inhibitors useful in the present invention include PD325901, PD-181461, ARRY142886/AZD6244, ARRY-509, XL518, JTP-74057, AS-701255, AS-701173, AZD8330, ARRY162, ARRY300, RDEA436, E6201, RO4987655/R-7167, GSK1120212 or AS703026.

In an important embodiment, the Mek 1/2 inhibitors include compounds described in WO03/077914, which is here incorporated by reference in its entirety, in particular a compound of formula (II) or (III).

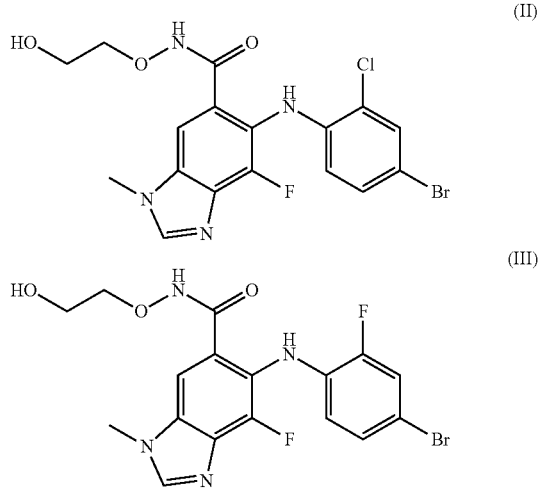

or pharmaceutically acceptable salts thereof, (hereinafter referred to as Compounds A and B, respectively) and the compounds described in WO05/051906, WO05/023251, WO03/077855, US20050049419, and U.S. Pat. No. 7,235,537, which are here incorporated by reference in their entirety, covering N3-alkylated benzimidazoles and other similar heterocyclic derivatives as Mek 1/2 inhibitors for the treatment of proliferative diseases.

CDK 4 inhibitors are known in the art and include flavopiridol, P1446A-05, LEE011, AT7519, BMS265246, LY2835219 and PD-0332991. In a particular embodiment of the present invention, the CDK 4 inhibitor is a compound disclosed in WO2007/140222 or WO 20210/020675, which are here incorporated by reference in their entirety. In a particular embodiment, the CDK 4 inhibitor is a compound of the formula (IV)

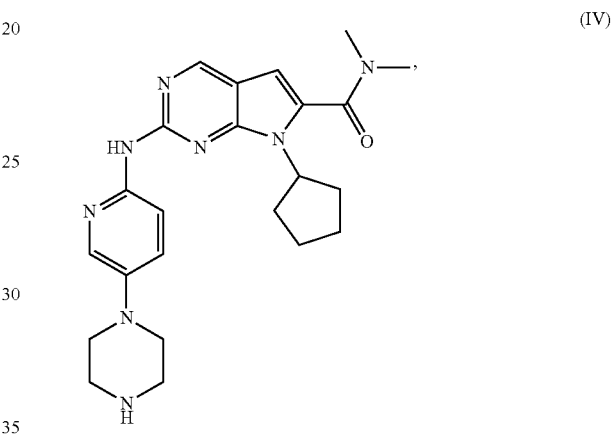

or a pharmaceutically acceptable salt thereof, hereinafter referred to as compound C.

PI3 Kinase inhibitors are known in the art and include perifosine, CAL-101, PX-866, BEZ235, SF1126, INK1117, GDC-0941, BKM120, XL147, XL765, Palomid529, GSK1059615, Zstk474, PTW33597, IC87114, TG100-115, CAL283, PI-103, BYL719, GNE-477, CUDC-907, and AEZS-136.

WO2006/122806, which is here incorporated by reference in its entirety, describes imidazoquinoline derivatives having PI3-kinase inhibitory activity. A very preferred compound of the present invention is 2-methyl-2-[4-(3-methyl-2-oxo-8-quinolin-3-yl-2,3-dihydro-imidazo[4,5-c]quinolin-1-yl)-phenyl]-propionitrile and its monotosylate salt (COMPOUND D). The synthesis of 2-methyl-2-[4-(3-methyl-2-oxo-8-quinolin-3-yl-2,3-dihydro-imidazo[4,5-c]quinolin-1-yl)-phenyl]-propionitrile is for instance described in WO2006/122806 as Examples 7 and 152-3. Another very preferred compound of the present invention is 8-(6-methoxy-pyridin-3-yl)-3-methyl-1-(4-piperazin-1-yl-3-trifluoromethyl-phenyl)-1,3-dihydro-imidazo[4,5-c]quinolin-2-one (COMPOUND E). The synthesis of 8-(6-methoxy-pyridin-3-yl)-3-methyl-1-(4-piperazin-1-yl-3-trifluoromethyl-phenyl)-1,3-dihydro-imidazo[4,5-c] quinolin-2-one is for instance described in WO2006/122806 as Example 86. WO07/084786 describes pyrimidine derivatives having PI3 Kinase inhibitory activity. A very preferred compound of the present invention is 5-(2,6-di-morpholin-4-yl-pyrimidin-4-yl)-4-trifluoromethyl-pyridin-2-ylamine (COMPOUND F). The synthesis of 5-(2,6-di-morpholin-4-yl-pyrimidin-4-yl)-4-trifluoromethyl-pyridin-2-ylamine is described in WO07/084786 as Example 10. Another preferred compound having PI3-kinase inhibitory activity is (S)-Pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (Compound X).

c-Met receptor tyrosine kinase inhibitors are known in the art and include crizotinib, PHA-665752, SU11274, PF-04217903, foretinib, SGX523, JNJ-38877605, GSK1363089, AMG208, and INCB28060. In a particular embodiment, the c-Met receptor tyrosine kinase inhibitor is a compound of the formula IV

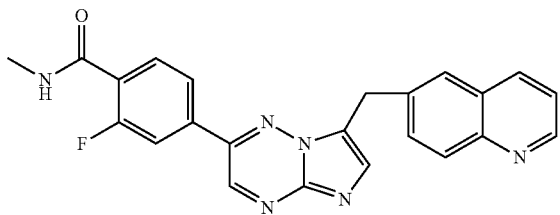 [SMILES: CNC(=O)c1ccc(-c2cnc3ncc(Cc4ccc5ncccc5c4)n3n2)cc1F]

or a pharmaceutically acceptable salt thereof, (hereinafter Compound G).

FGFR kinase inhibitors used according to the present method are preferably selective and ATP competitive pan FGFR kinase inhibitor including AZD4547 and BGJ398. In a particular embodiment, the FGFR kinase inhibitor is an aryl-pyrimidyl-urea derivative disclosed in WO2006/000420, particularly a compound of the formula (V)

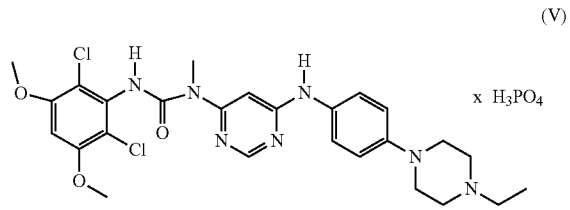 [SMILES: CCN1CCN(c2ccc(Nc3cc(N(C)C(=O)Nc4c(Cl)c(OC)cc(OC)c4Cl)ncn3)cc2)CC1]

or a pharmaceutically acceptable salt thereof (hereinafter Compound H).

Particular preference is given to embodiments of the inventive methods wherein the Mek 1/2 inhibitor is Compound A or Compound B, particularly compound B, the CDK 4 inhibitor is Compound C, the PI3 Kinase inhibitor is Compound D, Compound E, Compound F or Compound X, particularly Compound F, the c-Met receptor tyrosine kinase inhibitor is compound G and wherein the FGFR kinase inhibitor is Compound H, or a pharmaceutically acceptable salt of the aforementioned compounds.

The B-Raf inhibitor of Formula (I) is administered at a dose of 150 to 600 per day, preferably 400 to 600 per day, particularly 450 or 600 mg/day. As the second inhibitor of the drug combination therapy Compound B is administered at a dose of 15 to 60 mg BID, preferably 45 mg BID, Compound C is administered at a dose of 100 to 900 mg/day, preferably 200 to 900 mg/day, for example, 200, 400, 700 or 900 mg/day, Compound F is administered at a dose of 30 to 100 mg/day, preferably 60 to 100 mg/day or 60 to 80 mg/day, Compound G is administered at a dose of 50 to 300 mg BID, preferably 100 to 300 mg BID, for example, 100, 150, 200, 250 or 300 mg BID, or Compound H is administered at a dose of 25 to 125 mg/day, for example, 75, 100 or 125 mg/day.

In an important embodiment of the aforementioned methods, the genetic alteration in BRAF discovered in the tumor sample is other than a V600 mutation.

The present invention further relates to therapeutic combinations comprising a B-Raf inhibitor, preferably a B-Raf inhibitor of Formula (I) and a second inhibitor selected from the group consisting of a PI3 Kinase inhibitor, a c-Met receptor tyrosine kinase inhibitor and a FGFR kinase inhibitor for separate, simultaneous or sequential administration. More particularly, the therapeutic combination comprises a B-Raf inhibitor of Formula (I) and a second inhibitor which is a PI3 Kinase inhibitor selected from the group consisting of Compound D, Compound E, Compound F, and Compound X, or a pharmaceutically acceptable salt thereof; or the therapeutic combination comprises a B-Raf inhibitor of Formula (I) and a second inhibitor which is a c-Met inhibitor selected from Compound G, or a pharmaceutically acceptable salt thereof; or the therapeutic combination comprises a B-Raf inhibitor of Formula (I) and a second inhibitor which is a FGFR kinase inhibitor selected from Compound H, or a pharmaceutically acceptable salt thereof, for separate, simultaneous or sequential administration. Hereinafter, such therapeutic combinations are referred to as a COMBINATION OF THE INVENTION.

The present invention further relates to a method for treating a patient suffering from a proliferative disease characterized by a mutation in B-Raf, for example, melanoma characterized by a V600 mutation in B-Raf, which comprises, administering to the patient a therapeutically effective amount of a combination comprising a B-Raf inhibitor, preferably a B-Raf inhibitor of Formula (I) and a second inhibitor selected from the group consisting of a PI3 Kinase inhibitor, a c-Met receptor tyrosine kinase inhibitor and a FGFR kinase inhibitor. More particularly, the present invention relates to a method for treating a patient suffering from a proliferative disease characterized by a mutation in B-Raf, such as a V600 mutation, for example, melanoma characterized by a V600 mutation in B-Raf, which comprises, administering to the patient a therapeutically effective amount of a COMBINATION OF THE INVENTION. Preferably, these inhibitors are administered at therapeutically effective dosages which, when combined, provide a beneficial effect. The administration may be separate, simultaneous or sequential.

The present invention also pertains to a COMBINATION OF THE INVENTION for use in the preparation of a pharmaceutical composition or medicament for the treatment or prevention of a proliferative disease, particularly a proliferative disease characterized by a mutation in B-Raf, especially a V600 mutation in B-Raf, for example, melanoma characterized by a V600 mutation in B-Raf, in a patient in need thereof.

The present invention further provides a commercial package comprising as therapeutic agents a COMBINATION OF THE INVENTION, together with instructions for simultaneous, separate or sequential administration thereof for use in the delay of progression or treatment of a proliferative disease.

The administration of a COMBINATION OF THE INVENTION may result not only in a beneficial effect, e.g. a synergistic therapeutic effect, e.g. with regard to alleviating, delaying progression of or inhibiting the symptoms, but also in further surprising beneficial effects, e.g. fewer side-effects, more durable response, an improved quality of life or a decreased morbidity, compared with a monotherapy applying only one of the pharmaceutically therapeutic agents used in the combination of the invention.

The following examples are intended to illustrate, but not limit, the invention.

EXAMPLE 1

During the first part of the study, patients are treated with the B-Raf inhibitor of Formula (I) as a single agent at the Recommended Phase II Dose of 450 mg/day. The B-Raf inhibitor of Formula (I) is administered orally formulated as an encapsulated solid dispersion.

In the second part of the study, patients will be treated with the B-Raf inhibitor of Formula (I) in combination with a second targeted agent (i.e. the B-Raf inhibitor of Formula (I)+Compound B, the B-Raf inhibitor of Formula (I)+Compound F, the B-Raf inhibitor of Formula (I)+Compound H, the B-Raf inhibitor of Formula (I)+Compound G, or the B-Raf inhibitor of Formula (I)+Compound C). The dose escalation in each combination arm will be guided by a Bayesian logistic regression model (BLRM) in order to establish the MTD/RP2D of each combinations unless it has been previously determined in a separate combination trial. The open-label dose escalation study design using a BLRM is a well-established method to estimate the MTD(s) and/or RP2D(s) in cancer patients. The adaptive BLRM will be guided by the escalation with overdose control (EWOC) principle to control the risk of DLT in future patients on study. Intra-patient dose escalation will be permitted after the first cycle for patients who have not experienced a DLT.

Intra-patient dose escalation will be guided by the BLRM with a modified EWOC criteria that reflects individual patient tolerability. The use of Bayesian response adaptive models for small datasets has been accepted by EMEA and its development and appropriate use is one aspect of the FDA's Critical Path Initiative.

Rationale for Choice of Combination Drugs

Data from pre-clinical and clinical studies suggest that by simultaneous, dual, vertical pathway inhibition of the RAF/MEK/ERK signaling pathway with the B-Raf inhibitor of Formula (I) and Compound B combination could lead to increased clinical efficacy and possibly overcome early resistance to either single agent in patients with BRAF V600-dependent advanced melanoma. Moreover, other mechanisms that reactivate MAPK signaling or activate alternate pathways such as PI3K/AKT signaling pathway may play a role in primary and/or acquired resistance to BRAF inhibitors. Thus the antitumor activity of the B-Raf inhibitor of Formula (I) in combination with selected agent Compound F, Compound H, Compound G, and Compound C that target PI3K, c-met, FGFR and CDK4/6 kinase respectively, will also be assessed in addition to the B-Raf inhibitor of Formula (I)+Compound B. The selection of the B-Raf inhibitor of Formula (I) combination given to an individual patient will be based on the genetic alteration(s) identified in this patient's tumor sample upon the B-Raf inhibitor of Formula (I) progression (see table 1).

Description of Study Design

This is a multicenter, open-label, phase II study which will enroll approximately 100 patients with BRAF mutant locally advanced or metastatic melanoma, and consists of two treatment parts.

In the first part, Part I, patients naïve to a selective BRAF inhibitor will be treated with the B-Raf inhibitor of Formula (I) single agent at the RP2D of 450 mg/day until disease progression (as defined per RECIST v1.1). At the time of disease progression, the tumor will be biopsied and analyzed for a selected panel of genes (Table 1).

The patients relapsing in Part I of the study will continue to receive the B-Raf inhibitor of Formula (I) single agent, during the expected turn-around time for the molecular analysis of the resistance biopsy, until the appropriate the B-Raf inhibitor of Formula (I) rational combination can be identified and initiated.

Based upon genetic alterations identified from the tumor biopsy at relapse, cohorts of patients will enter in the second part of the study, Part II, for a tailored combination treatment of the B-Raf inhibitor of Formula (I) plus a second targeted agent. There will be 5 arms corresponding to the 5 combination treatment studied: the B-Raf inhibitor of Formula (I)+Compound B, the B-Raf inhibitor of Formula (I)+Compound F, the B-Raf inhibitor of Formula (I)+Compound H, the B-Raf inhibitor of Formula (I)+Compound G, and the B-Raf inhibitor of Formula (I)+Compound C. The selection of the second agent will be defined following Table 1 criteria. It is anticipated that more than half of the patients enrolled will receive a combination treatment of the B-Raf inhibitor of Formula (I) plus Compound B after progression on the B-Raf inhibitor of Formula (I).

Non-naïve patients for BRAF inhibitor treatment who are relapsing in a prior study in which patients with BRAF V600 mutant melanoma were treated with the B-Raf inhibitor of Formula (I) single agent can be enrolled after progression on the B-Raf inhibitor of Formula (I) single agent in Part II. For these patients, the analysis results of the fresh tumor biopsy collected at the End of Treatment visit from the previous trial will be used for combination treatment assignment in Part II.

The patients relapsing in other the B-Raf inhibitor of Formula (I) single agent studies (e.g IIT), will be discontinued from the the B-Raf inhibitor of Formula (I) treatment after progression and will stop receiving the B-Raf inhibitor of Formula (I) single agent, until they can be assigned to a rational combination treatment in part II of the study.

Progressive disease of those patients is deemed to be confirmed from the previous study and will be used as baseline tumor evaluation for Part II of the study if a time interval before the CT at progression and the start of study treatment within this study is no longer than 28 days.

All patients will start the rational combination at the defined dual combination MTD/RP2D, or if the dual combination MTD/RP2D has not been previously determined, at the RP2D of 450 mg/day for the B-Raf inhibitor of Formula (I) (or the highest last-dose tolerated by the patient) in combination with the second agent at a starting dose allowed by the Bayesian logistic regression model. The rational combination treatment part will continue with the possibility of ascending dose of the second agent until a MTD/RP2D of the combination has been established. Intra patient dose escalation of the second agent guided by a BLRM will be allowed under pre-defined conditions for patients who tolerated the combination at a given dose for at least one cycle.

Combination treatment will be administered in 21-day cycles until disease progression, where the tumor assessments during combination treatment will be compared to a recalculated baseline (i.e., the result of tumor evaluation leading to PD assessment on the B-Raf inhibitor of Formula (I) single agent treatment either in part I or in previous study).

Molecular Pre-Screening

To enter the screening phase of the study, patients must have written documentation of BRAF V600 mutation, which should be obtained locally on a fresh tumor biopsy (preferred) or the most recent archival tumor sample available. However, patients for whom molecular status is not known at the time of consideration for enrollment in this study and who have a tumor which is not routinely screened for a BRAF mutation at a local laboratory and for whom fresh tumor collection is required, will sign a molecular pre-screening Informed Consent allowing for the collection of fresh tumor sample for local assessment of the mutational status. Only once the BRAF V600 mutational status is known or determined, the patient is allowed to sign the main Study Informed Consent Form and start screening.

Screening

Once the BRAF V600 mutational status is known or determined, the patient is allowed to sign the Main Study Informed Consent Form and start screening. All screening evaluations are required to be performed before administration of study treatment.

Treatment Period

There will be two treatment parts: Part I and Part II:

Part I=the single agent treatment phase and will begin on Cycle 1 Day 1 until initiation of combination treatment.

Part II=the combination treatment, should be initiated once the genetic alterations from tumor biopsy collection at the time of relapse are known.

Study treatments will be administered during 21-day cycles and will continue until disease progression (on dual combination treatment), unacceptable toxicity, withdrawal of informed consent, or death.

Patient Population

The study will be conducted in adult patients with locally advanced or metastatic melanoma harboring a confirmed BRAF V600 mutation, Patients enrolled in the first part of the trial (Part I) must be naïve to a selective BRAF inhibitor.

Patients previously treated with the B-Raf inhibitor of Formula (I) single agent can be enrolled directly in Part II if a tumor biopsy is collected at the time of relapse.

Patients enrolled in this study are not permitted to participate in parallel investigational drug or device studies. Additionally, patients who have completed the study must not be re-enrolled for a second course of treatment.

The investigator or designee must ensure that only patients who meet all the following inclusion and none of the exclusion criteria are offered treatment in the study.

Inclusion Criteria

Patients naïve for the B-Raf inhibitor of Formula (I) (eligible for Part I).

Patients eligible for inclusion in the study have to meet all of the following criteria:

Age ≥18 years at the start of dosing

Able to understand and voluntarily sign the informed consent form, and ability to comply with the study visit schedule and other protocol requirements. Written informed consent must be obtained prior to screen procedures Histologically confirmed diagnosis of unresectable stage III or metastatic melanoma (stage IIIC to IV per American Joint Committee on Cancer [AJCC]).

Written documentation of BRAF V600 mutation,

Fresh tumor biopsy at baseline, and patient agrees for a mandatory biopsy at the time of relapse, if not medically contraindicated.

Evidence of measurable disease, as determined by RECIST v1.1.

Note: Lesions in areas of prior radiotherapy or other locoregional therapies (e.g., percutaneous ablation) should not be considered measurable, unless lesion progression has been documented since the therapy.

Life expectancy ≥3 months

World Health Organization (WHO) Performance Status ≤2.

Negative serum pregnancy test within 72 hours prior to the first dose of study treatment in all women of childbearing potential.

A mandatory fresh biopsy at relapse after the B-Raf inhibitor of Formula (I) single agent treatment must be available.

The patients of in other single agent studies of the B-Raf inhibitor of Formula (I) with documented progressive disease could join the Part II according the resistance profile results which will determine the combination arm assignment for treatment.

Progressive disease of those patients has to be confirmed from the previous study with a tumor evaluation assessment. If the time interval between the tumor evaluation documenting the disease progression and the first dose of the combination treatment is more than 4 weeks (28 days), a new tumor evaluation should be performed. The biopsy performed at the End of Treatment visit of the previous study and characterized through a comprehensive genomic analysis will be required for the assignment of the combination treatment.

Exclusion Criteria

Patients eligible for this study must not meet any of the following criteria:

Enrollment in Part I (the B-Raf inhibitor of Formula (I) single agent treatment):

Previous treatment with RAF-inhibitor

Symptomatic or Untreated Leptomeningeal Disease

Symptomatic brain metastases. Patients previously treated or untreated for these conditions that are asymptomatic in the absence of corticosteroid therapy are allowed to enroll. Brain metastasis must be stable at least three months with verification by imaging (e.g. brain MRI or CT completed at screening demonstrating no current evidence of progressive brain metastases). Patients are not permitted to receive enzyme inducing anti-epileptic drugs.

Known Acute or Chronic Pancreatitis

Clinically significant cardiac disease including any of the following:

CHF requiring treatment (NYH grade ≥2), LVEF <45% as determined by MUGA scan or ECHO, or uncontrolled hypertension (please refer to WHO-ISH guidelines)

History or presence of clinically significant ventricular arrhythmias or atrial fibrillation Clinically Significant Resting Bradycardia Unstable angina pectoris ≤3 months prior to starting study drug Acute Myocardial Infarction (AMI)≤3 months prior to starting study drug QTcF >480 msec on screening ECGs Patients with any of the following laboratory values at baseline:

Absolute neutrophil count (ANC) <1,500/mm3 [1.5×109/L]

Platelets <100,000/mm3 [100×109/L]

Hemoglobin <9.0 g/dL

Serum creatinine >1.5×ULN

Serum total bilirubin >1.5×ULN

AST/SGOT and ALT/SGPT >2.5×ULN, or >5×ULN if liver metastases are present

Impairment of gastrointestinal (GI) function or GI disease that may significantly alter the absorption of oral interventional drug (e.g., ulcerative diseases, uncontrolled nausea, vomiting, diarrhea, malabsorption syndrome, small bowel resection).

Previous or concurrent malignancy. Exceptions: adequately treated basal cell or squamous cell skin cancer; in situ carcinoma of the cervix, treated curatively and without evidence of recurrence for at least 3 years prior to study entry; or other solid tumor treated curatively, and without evidence of recurrence for at least 3 years prior to study entry.

History of thromboembolic or cerebrovascular events within the last 6 months, including transient ischemic attack, cerebrovascular accident, deep vein thrombosis, or pulmonary embolism.

Patients who have received radiation therapy (that includes >30% of the bone marrow reserve), chemotherapy, biological therapy (e.g., antibodies) within ≤4 weeks (6 weeks for nitrosourea, mitomycin-C), or who have been treated with continuous or intermittent small molecule therapeutics or investigational agents within 5-half-lives of the agent (or ≤4 weeks when half-life is unknown) prior to starting study drug or who have not recovered from the side effects of such therapy (except alopecia).

Patients who have undergone any major surgery within the last 2 weeks prior to starting study drug or who would not have fully recovered from previous surgery.

Known Human Immunodeficiency Virus (HIV) Infection.

Other severe, acute, or chronic medical or psychiatric condition or laboratory abnormality that may increase the risk associated with study participation or study drug administration or that may interfere with the interpretation of study results and, in the judgment of the investigator, would make the patient inappropriate for the study.

Pregnant or nursing (lactating) women, where pregnancy is defined as the state of a female after conception and until the termination of gestation, confirmed by a positive hCG laboratory test (>5 mIU/mL). Women of child-bearing potential, defined as all women physiologically capable of becoming pregnant, are not allowed to participate in this study UNLESS they are using highly effective methods of contraception throughout the study and for 10 days after study drug discontinuation.

Post-menopausal women are allowed to participate in this study. Women are considered post-menopausal and not of child bearing potential if they have had 12 months of natural (spontaneous) amenorrhea with an appropriate clinical profile (e.g. age appropriate, history of vasomotor symptoms) or six months of spontaneous amenorrhea with serum Follicle-Stimulating Hormone (FSH) levels >40 mIU/mL or have had surgical bilateral oophorectomy (with or without hysterectomy) or tubal ligation at least six weeks prior to screening. In the case of oophorectomy alone, only when the reproductive status of the woman has been confirmed by follow-up hormone level assessment is she considered not of child bearing potential.

Sexually active males must use a condom during intercourse while taking the drug and for 3 months after stopping treatment and should not father a child in this period. A condom is required to be used also by vasectomized men in order to prevent delivery of the drug via seminal fluid.

Study Treatment

The investigational drugs to be used in this study are the B-Raf inhibitor of Formula (I), Compound B, Compound F, Compound H, Compound G, and Compound C.

The study treatments are:
Part I: single agent the B-Raf inhibitor of Formula (I)
Part II: dual combinations
the B-Raf inhibitor of Formula (I) (QD) and Compound B (BID)
the B-Raf inhibitor of Formula (I) (QD) and Compound F (QD)
the B-Raf inhibitor of Formula (I) (QD) and Compound H (QD)
the B-Raf inhibitor of Formula (I) (QD) and Compound G (BID)
the B-Raf inhibitor of Formula (I) (QD) and Compound C (QD)

Dosing Regimens

TABLE 2

Dose and treatment schedule

| Study treatments | Pharmaceutical form and route of administration | Starting Dose (21 days cycles) |
|---|---|---|
| the B-Raf inhibitor of Formula (I) | Capsule for oral use | 450 mg/day, or highest tolerated dose |
| Compound B | Tablet for oral use | 45 mg BID |
| Compound F | Capsule for oral use | 60 mg |
| Compound H | Capsule for oral use | 75 mg |
| Compound G | Capsule for oral use | 150 mg BID |
| Compound C | Capsule for oral use | 200 mg |

Instructions for Administration of the B-Raf Inhibitor of Formula (I)+Second Agent The B-Raf inhibitor of Formula (I), Compound F, Compound H and Compound C will be administered orally on a daily schedule (QD) as a flat-fixed dose, and not by body weight or body surface area.

QD Dosing: Patients should be instructed to take the B-Raf inhibitor of Formula (I) (and Compound F, Compound H or Compound C) capsules daily with a large glass of water (~250 ml) in the morning. On all dose administrations patients should fast for 2 hours prior to and after study drug intake. If the patient forgets to take the dose in the morning, then he/she should take the dose within 6 hrs after the missed dose. If more than 6 hours has passed, then the dose should be withheld that day and the patient should continue treatment with the next scheduled dose. If, for any reason, a breakfast was not consumed, then the patient should still take the scheduled morning dose with a glass of water. If this happens on days of full PK sampling, it should be documented.

Compound B and Compound G will be administered orally on a twice daily schedule (BID) as a flat-fixed dose, and not by body weight or body surface area.

BID Dosing: The doses of Compound B, or Compound G, should be taken 12±2 hours apart. Patients will be instructed to take doses daily with a large glass of water (~250 ml) in the morning and in the evening. For the B-Raf inhibitor of Formula (I) and Compound G combination, on all dose administrations patients should fast for 2 hours prior to and after study drug intake. For the B-Raf inhibitor of Formula (I) and Compound B combination, on all morning dose administration days patients should not eat anything within 2 hours prior to study drug intake and refrain from eating for 2 hours following the B-Raf inhibitor of Formula (I) and Compound B intake. On all evening dose administrations patients should fast for 1 hour prior to and after Compound B intake Note that both drugs (the B-Raf inhibitor of Formula (I)+Compound B, or Compound G) should be taken together in the morning and only the BID administered drug (Compound B, or Compound G) should be taken in the evening.

Instructions for Administration on Days when a PK Sampling is Performed:

Pre-dose PK samples should be collected just prior to intake of dose.

At each visit, responsible site personnel will ensure that the appropriate dose of each study drug is administered and will provide the patient with the correct amount of study drug(s) for subsequent dosing. Patients will be instructed to return unused study drugs to the site at each visit.

Patients should be instructed to swallow the capsules/tablets whole and not to chew or crush them.

Any doses that are skipped should not be replaced or made up during the next scheduled dosing or on a subsequent day, whichever applies.

Patients must avoid consumption of grapefruit, pomegranates, star fruits, Seville oranges or products containing the juice of each during the entire study and preferably 7 days before the first dose of study medications, due to potential CYP3A4 interaction with the study medications. Orange juice is allowed.

If vomiting and/or diarrhea occurs during the course of treatment, no re-dosing of the patient is allowed before the next scheduled dose. The occurrence and frequency of any vomiting and/or diarrhea (or increased stool frequency) within 4 hours after dosing must be noted in the AEs section of the eCRF. In addition, on the days of full PK sampling, the onset time of any episodes of vomiting within the first 4 hours post-dosing on that day must be noted in the corresponding Dose Administration Record PK eCRF.

The investigator or responsible site personnel should instruct the patient to take the study drugs as per protocol (promote compliance). All dosages prescribed and dispensed to the patient and all dose changes and all missed doses during the study must be recorded on the Dosage Administration Record eCRF. Drug accountability must be performed on a regular basis. Patients will be instructed to return unused study drugs to the site at the end of each cycle. The site personnel will ensure that the appropriate dose of each study drug is administered at each visit and will provide the patient with the correct amount of drugs for subsequent dosing.

For the combination arm of the B-Raf inhibitor of Formula (I) with Compound F only Instructions for administration on days when a fasting plasma glucose monitoring is performed: On the days of fasting plasma glucose monitoring, patients must be fasting overnight for at least 8 hours prior to the blood collection. A light breakfast/snack may be consumed after fasting plasma glucose draw. the B-Raf inhibitor of Formula (I) (and Compound F if applicable) may be administered 2 hours after breakfast. Patients should continue to fast for 2 hours after the administration of the B-Raf inhibitor of Formula (I) (and Compound F if applicable).

Treatment Duration

Patients may continue treatment with the B-Raf inhibitor of Formula (I) single agent until experiencing unacceptable toxicity, and/or the treatment is discontinued at the discretion of the investigator or withdrawal of consent. At disease progression, after the B-Raf inhibitor of Formula (I) single agent treatment, patients will be assigned to a combination treatment according to genetic alterations identified in the relapse biopsy. Patients may continue combination treatment until experiencing unacceptable toxicity, disease progression and/or the treatment is discontinued at the discretion of the investigator or withdrawal of consent.

Dose Escalation Guidelines

Starting dose rationale.

The B-Raf Inhibitor of Formula (I) Single Agent

The dose for the B-Raf inhibitor of Formula (I), for patients enrolled in the first part of this trial, is set at 450 mg QD, which corresponds to the single agent RP2D. The selection of the starting dose follows the ICH S9 guidelines for choosing a starting a dose for a first-in-human trial conducted in patients with cancer, and is shown in Table 6-2.

The B-Raf Inhibitor of Formula (I) in Combination with Compound B:

The starting dose for the B-Raf inhibitor of Formula (I) plus Compound B, is set at the B-Raf inhibitor of Formula (I) 600 mg QD and Compound B 45 mg BID, or the highest dose combination proven to be safe.

The B-Raf Inhibitor of Formula (I) in Combination with Second Agent (Compound F, Compound H, Compound G or Compound C):

In the second part of this trial, the starting doses for the B-Raf inhibitor of Formula (I) and second agent will be respectively 450 mg QD (RP2D), or the highest last-dose tolerated of the B-Raf inhibitor of Formula (I) and the highest dose of the second agent allowed by the BLRM (see Table 3).

The RP2D of the B-Raf inhibitor of Formula (I) has been declared at 450 mg QD.

Qualitative DDI assessment predicts no significant impact on the B-Raf inhibitor of Formula (I) or Compound F exposure when they are co-administered. Quantitative analysis using SimCYP simulation confirmed this assessment. Therefore the starting dose for this combo pair is selected to be the currently established RP2D for the B-Raf inhibitor of Formula (I) and 75% MTD for Compound F: 450 mg QD the B-Raf inhibitor of Formula (I) and 75 mg Compound F.

Quantitative DDI assessment using Simcyp simulation predicts minimal changes in the B-Raf inhibitor of Formula (I) exposure when co-administered with Compound H. At the B-Raf inhibitor of Formula (I) dose of 450 mg, the exposure (Cmax and AUC) of Compound H is expected to decrease by 20-40%. Therefore the starting dose for this combo pair is selected to be the currently established RP2D for the B-Raf inhibitor of Formula (I) and 60% MTD for Compound H: 450 mg QD the B-Raf inhibitor of Formula (I) and 75 mg Compound H.

Quantitative DDI assessment using Simcyp simulation predicts 76% and 43% increase in AUC and Cmax of the B-Raf inhibitor of Formula (I), respectively, as well as 54% and 36% decrease in AUC and Cmax of Compound G, respectively when 450 mg QD the B-Raf inhibitor of Formula (I) and 150 mg BID Compound G are co-administered. In clinic, the B-Raf inhibitor of Formula (I) has been tested at up to 700 mg QD dose and the observed adverse events are reversible and manageable, therefore the potential DDI between the two molecules while may result in the B-Raf inhibitor of Formula (I) concentrations higher than the currently established RP2D, do not pose a risk as the adverse events are monitorable, manageable and reversible. The starting dose for this combo pair is selected to be the currently established RP2D for the B-Raf inhibitor of Formula (I) and 50% MTD for Compound G: 450 mg QD the B-Raf inhibitor of Formula (I) and 150 mg Compound G.

Quantitative DDI assessment using Simcyp simulation predicts 43% and 20% increase in AUC and Cmax of the B-Raf inhibitor of Formula (I), respectively, as well as 43% and 37% decrease in AUC and Cmax of Compound C, respectively when 450 mg QD the B-Raf inhibitor of Formula (I) and 300 mg Compound C are co-administered. In clinic, the B-Raf inhibitor of Formula (I) has been tested at up to 700 mg QD dose and the observed adverse events are reversible and manageable, therefore the potential DDI between the two molecules while may result in the B-Raf inhibitor of Formula (I) concentrations higher than the currently established RP2D, do not pose a risk as the adverse events are monitorable, manageable and reversible. The starting dose for this combo pair is selected to be the currently established RP2D for the B-Raf inhibitor of Formula (I) and ~23% of the dose currently tested at the 900 mg QD dose level, since the maximum tolerated dose (MTD) has not been achieved for Compound C: 450 mg QD the B-Raf inhibitor of Formula (I) and 200 mg Compound C.

In this study, the pharmacokinetics of all combination partners as well as their active metabolites (if applicable) will be evaluated as soon as possible at steady-state and compared with those obtained in the respective monotherapy studies for assessment of the potential drug-drug interaction Before the first patient is dosed with one of the combinations, the Bayesian model for this combination will be updated with the most recent data from the ongoing single agent trial, to confirm that the proposed starting doses for the B-Raf inhibitor of Formula (I) and second agent are still appropriate (i.e. fulfills the EWOC criteria). If the proposed starting dose does not meet the criteria, a lower dose combination that satisfies the EWOC criteria will be used.

Provisional Dose Levels

Table 3 describes the starting doses and the provisional dose levels of study treatments for the combinations that may be evaluated during this trial. Additional dose levels not currently specified may be enrolled and additional patients may be enrolled at a dose level already tested if such changes are deemed necessary to provide optimal safety and tolerability, pharmacokinetic, and pharmacodynamic data.

TABLE 3

Provisional dose levels

| Dose level* (mg) | B-Raf inhibitor QD | Cpd B BID | Cpd F QD | Cpd H QD | Cpd G BID | Cpd C QD |
|---|---|---|---|---|---|---|
| −2** | 150 | 15 | 30 | 25 | 50 | 100 |
| −1** | 300 | 30 | 40 | 50 | 100 | 150 |
| 1 (starting dose) | 450 (600 for Compound B arm) | 45 (RP2D) | 60 | 75 | 150 | 200 |
| 2 | 450 | — | 80 | 100 | 200 | 400 |
| 3 | 450 | — | 100 (MTD) | 125 (MTD) | 250 | 700 |
| 4 | 450 | — | — | — | 300 | 900 |

*It is possible for additional and/or intermediate dose levels to be added during the course of the study Cohorts may be added at any dose level below the MTD in order to better understand safety, PK or PD.
**Dose level −1 and −2 will also be used for patients requiring a dose reduction from the starting dose level. No dose reduction below dose level −2 is permitted for this study.

Implementation of Dose Escalation Decisions

The decision to escalate the dose of the second agent will occur after evaluation of the individual patient tolerability of the dual combination during the first 21 days of the cycle.

To implement dose escalation decisions, the available toxicity information (including adverse events and laboratory abnormalities that are not DLTs), the recommendations from the BLRM, and the available PK and PD information will all be evaluated during a dose decision. Drug administration at the next higher dose level may not proceed until the investigator receives written confirmation indicating that the results of the previous dose level were evaluated and that it is permissible to proceed to a higher dose level. If a decision is made to escalate to a higher dose level but one or more additional patient(s) treated at the preceding dose level experiences a DLT during the first cycle of treatment, then the BRLM will be updated with this new information before any additional patients are enrolled at that higher dose level.

The dose escalation process will be implemented stepwise and will proceed with cohorts of 3 patients. Only the second agent, Compound F, Compound H, Compound G, or Compound C will be escalated according to the BLRM.

Intra-patient dose escalation is not permitted at any time within the part I of treatment with the B-Raf inhibitor of Formula (I) single agent.

Intra-patient dose escalation for second agent is permitted during the second part with the combination treatment with the exception of patients in the the B-Raf inhibitor of Formula (I)+Compound B arm, who will be treated at the declared RP2D of the combination of the B-Raf inhibitor of Formula (I) and Compound B (45 mg BID)

In order for a patient to be treated at a higher dose of Compound F, Compound H, Compound G, or Compound C, he or she must have tolerated the lower dose combination for at least 1 cycle of therapy (e.g., he or she must not have experienced at the lower dose pair originally assigned a toxicity of CTCAE grade ≥2 for which relationship to study drugs cannot be ruled out). Moreover, the new, higher dose pair with which the patient is to be treated must meet the modified EWOC criteria used for intra-patient escalation (add ref to section).

Newly enrolled patients in the next cohort will start treatment at the dose decided at the last dose escalation conference. The Bayesian logistic regression model (BLRM) and the intra-patient dose boundaries will then be updated for the next cohort.

Treatment Interruption and Treatment Discontinuation

If a patient requires a dose delay of >21 consecutive days of the B-Raf inhibitor of Formula (I), Compound B, Compound F, Compound H, Compound C, or Compound G from the intended day of the next scheduled dose, then the patient should be discontinued from the study treatment. In exceptional situations, if the patient is clearly benefiting from the study treatment (i.e. stable disease, partial response, complete response), and in the opinion of the investigator no safety concerns are present, the patient may remain on the study treatment at a dose level adjusted based on safety.

Molecular Pre-Screening

Molecular Pre-Screening Informed Consent

The molecular pre-screening informed consent must be signed prior to any study-related molecular pre-screening procedure (not applicable if the mutational status of BRAF was already assessed outside of the study). This applies to Part 1 patients only.

BRAF Mutational Status on Fresh or Archival Biopsy

To enter the screening phase of the study, patients must have written documentation of BRAF V600 mutation, which should be obtained locally on a fresh tumor biopsy (preferred) or the most recent archival tumor sample available. The molecular pre-screening informed consent must be signed prior to any study-related molecular pre-screening procedure (not applicable if the mutational status was already assessed outside of the study).

Once the mutation of the BRAF V600 codon (e.g. V600E/K/D/R) is confirmed by the designated local laboratory and documented by the site, the patient may begin the screening procedures.

Treatment Period

Treatment period is divided into two parts:

Part I: BRAF inhibitor naïve patients will be dosed continuously with the B-Raf inhibitor of Formula (I) on 21-day (3 calendar weeks) cycles beginning on Day 1 of Cycle 1. There will be no scheduled break between cycles. Patients will receive the B-Raf inhibitor of Formula (I) single agent until initiation of combination treatment after progression of disease or unacceptable toxicity occurs, whichever comes first.

Part II: Patients who received the B-Raf inhibitor of Formula (I) for at least one 21-day cycle and who progressed will enter in the Part II to receive a treatment combination of the B-Raf inhibitor of Formula (I)+second agent, based upon the genetic alterations identified in the tumor biopsy at relapse.

There is no fixed treatment duration; patients may continue treatment with the B-Raf inhibitor of Formula (I) single agent until combination treatment and during first disease progression, unacceptable toxicity occurs that precludes any further treatment and/or treatment is discontinued at the discretion of the investigator or by patient refusal (withdrawal of consent). At the time of first disease progression, once biopsy's analysis results are known, patients may initiate combination treatment with the B-Raf inhibitor of Formula (I)+second inhibitor until secondary disease progression, unacceptable toxicity occurs that precludes any further treatment and/or treatment is discontinued at the discretion of the investigator or by patient refusal (withdrawal of consent) If a patient remains on study although the patient required a dose interruption of >21 days, because the patient had experienced objective evidence of clinical benefit and in the opinion of the investigator it is in the best interest of the patient to remain on study.

Bayesian Logistic Regression Model

An adaptive BLRM guided by the EWOC principle will guide the dose escalation of each of the study drugs (Compound F, Compound H, Compound G or Compound C) combined with the B-Raf inhibitor of Formula (I) to its respective MTD(s)/RP2D(s). For each combination, a 5-parameter BLRM for combination treatment will be fitted on the Cycle 1 dose-limiting toxicity data (i.e. absence or presence of DLT) accumulated throughout the dose escalation to model the dose-toxicity relationship of Compound F, Compound H, Compound G or Compound C given in combination with the B-Raf inhibitor of Formula (I).

The definition of the BLRM's, the prior distributions for the model parameters (based on currently available information about the targeted agents) and the associated prior distribution of DLT rates are provided in Appendix 1.

Dose Recommendation

Dose recommendation for the combination partner is conditional to the dose of the B-Raf inhibitor of Formula (I) which may differ between patients entering Part II. This recommendation will be based on posterior summaries of the DLT rate including the mean, median, standard deviation, 95%-credibility interval, and the probability that the true DLT rate for each dose combination lies in one of the following categories:

[0%, 16%] under-dosing
[16%, 35%] targeted toxicity
[35%, 100%] excessive toxicity Following the principle of EWOC, after each cohort of patients the recommended dose combination is the one with the highest posterior probability of DLT in the target interval [16%, 35%] among the doses fulfilling the overdose criterion that there is less than 25% chance of excessive toxicity.

In addition, the maximum inter-cohort combined dose escalation across the two study drugs is limited to 100%, where 100% refers to the sum of the relative escalation for each of the study drugs, i.e. 0% and 100% for the B-Raf inhibitor of Formula (I) (which dose cannot exceed 450 mg) and for the second targeted agent (which cannot be escalated beyond its s.a. MTD/RP2D if available), respectively.

The Intra-patient dose escalation of the combination partner will be limited to 50% and will be guided by the BLRM according to the following modified EWOC criterion which reflects individual patient tolerability: a patient will be able to intra-escalate to a dose for which there is less than a 40% chance of excessive toxicity. Furthermore, if treatment-related toxicities of CTCAE grade 2 are observed in 2 or more patients at a dose level or if any patient experiences a grade 3 or greater toxicity, then the increase in dose of the combination partner will be ≤25% for any subsequent increase in dose.

A clinical synthesis of the available toxicity information (including AEs that are not DLTs), PK, PD, and efficacy information as well as the recommendations from the Bayesian model will be used to determine the dose combination for the next cohort at a dose-escalation conference. The Investigators and trial personnel will be involved in the decision making.

The model for any combination will be re-evaluated before enrollment of any additional patients to the cohort if the first 2 evaluable patients in the cohort experience DLT before the enrollment of the 3rd patient. The final recommended MTD/RP2D for each combination will be based on considerations of the recommendation from the BLRM, and on an overall assessment of safety taking into consideration tolerability data from subsequent cycles at all different dose combinations tested.

EXAMPLE 2

Materials and Methods

Compound stocks are prepared in DMSO at a final concentration of 10 mM. Working stocks are serially diluted in the appropriate cell culture medium in 3-fold increments to achieve final assay concentrations ranging from 2.71M to 1.2 nM.

Cell Lines, Cell Culture, Cell Viability Measurements

A-375 and WM-266-4 cells were purchased from American Type Culture Collection (ATCC). The A-375 cells were cultured in DMEM medium (ATCC) and the WM-266-4 cells were cultured in EMEM medium (ATCC) both supplemented with 10% fetal bovine serum (Gibco) and incubated at 37° C./5% CO2. The cell lines engineered to express commonly occurring alleles indicative of resistance were acquired from Novartis-Emeryville. These resistant models include, A-375 cells expressing mutant MEK1P124L, truncated p61-BRAFV600E, or mutant NRASQ61K, and WM-266-4 cells expressing mutant MEK1C121S, truncated p61-BRAFV600E, or mutant NRASQ61K. These cells were cultured in the appropriate parental medium with selection marker G418 and in the presence of 5 uM LFE158 (MEK mutants) or LIH720 (truncated p61-BRAFV600E).

Plate Layout, Cell Dispensing and Compound Addition

For screening, cells were seeded in 80 ul of medium in 384-well plates (Thermo Scientific, cat#4332) at 500 (A-375) or 750 (WM-266-4) cell densities per well using a MultiDrop Combi (Thermo-Fisher) with an 8-channel standard cassette. To promote an even distribution of cells across the entire well, cells were briefly centrifuged at 1000 RPM and incubated at room temperature 30 minutes. All plates were incubated at 37° C., 5% CO2 for 24 h prior to compound addition. Compound stock was freshly prepared in the appropriate culture medium, and added using a PAA robot equipped with a 200 nl pin tool. In a minimum of three replicate wells, single agent and combination effects after 72 hours, were assessed by both quantification of cellular ATP levels via Cell Titer Glo (Promega) according to the manufacturer's protocol and by microscopy imaging. For imaging, cells were fixed to the plates and permeabilized with a solution of 10% PFA, 0.3% TX-100 in PBS via a WellMate dispenser with controlled dispensing speeds. Cell nuclei were stained with Hoechst 33342 (H3570, Invitrogen), and all necessary washing steps were performed by a BioTek washer.

Automated Image Analysis

Images from the InCell Analyzer 2000 (GE Healthcare, 28-9534-63) were in TIFF format and had a size of 2048× 2048 pixels, capturing the whole well of a 384-well plate. An automated image analysis pipeline was established using custom-made scripts in the open-source, statistical programming language R, and functions of the BioConductor package EBImage. The goal was to quantify the number of viable nuclei (cells) per well as an approximation for cell viability. The pipeline was comprised of seven steps: (I.) smoothing of the image to reduce the number of intensity peaks, (II.) application of a thresholding function to separate the foreground (signal) from the background (noise), (Ill.) identification of local maxima in the foreground that serve as seeds for the nuclei, (IV.) filtering of local maxima in close proximity, (V.) propagation of the nuclei from remaining local maxima, (VI.) and extraction of object features from the propagated nuclei (numbers of nuclei, size features and intensity features). As a last step (VII.), to exclude debris (e.g. fragmented nuclei) from counting, objects identified in DMSO- and Staurosporin-treated wells were used to obtain feature distributions for viable and fragmented nuclei, respectively. These were used to set cut-offs differentiating between viable and fragmented nuclei. The number of fragmented nuclei was subtracted from the total number of identified objects and the result was reported as final count for that well.

Data Normalization

Data comprised triplicate measurements for each treatment (compound) condition, 42 replicates of DMSO-treated wells, and duplicates of Staurosporin-treated wells. The data was normalized to the median of the DMSO measurements and summarized by calculating the median of the triplicates. Data was imported into Chalice to calculate compound synergies.

TABLE 4

Chart of Single Agent IC50 Values and Combination Synergy Scores as determined using ATP-based CTG assay

| Parent Cell Line | Resistant Allele | Cpd. of Formula (I) IC50 (nM) | Cpd. B IC50 (nM) | Combination Lowe Excess Synergy |
|---|---|---|---|---|
| A-375 | — | 4 | 51 | 3.0 |
| A-375 | MEK1$^{P124L}$ | 333 | >2700 | 7.8 |
| A-375 | p61 BRaf$^{V600E}$ | 576 | 961 | 4.6 |
| A-375 | NRAS$^{Q61K}$ | 134 | 206 | 4.3 |
| WM-266-4 | — | 2 | 50 | 4.2 |
| WM-266-4 | MEK1$^{C121S}$ | 35 | 821 | 5.4 |
| WM-266-4 | p61 BRaf$^{V600E}$ | 906 | >2700 | 5.8 |
| WM-266-4 | NRAS$^{Q61K}$ | 1122 | >2700 | 5.1 |

TABLE 5

Chart of Single Agent IC50 Values and Combination Synergy Scores as determined using microscopy assay

| Parent Cell Line | Resistant Allele | Cpd. of Formula (I) IC50 (nM) | Cpd. B IC50 (nM) | Combination Lowe Excess Synergy |
|---|---|---|---|---|
| A-375 | — | 4 | 57 | 2.4 |
| A-375 | MEK1$^{P124L}$ | 300 | >2700 | 9.3 |
| A-375 | p61 BRaf$^{V600E}$ | 849 | 969 | 5.9 |
| A-375 | NRAS$^{Q61K}$ | 133 | 150 | 4.6 |
| WM-266-4 | — | 3 | 77 | 4.7 |
| WM-266-4 | MEK1$^{C121S}$ | 58 | 1210 | 6.3 |
| WM-266-4 | p61 BRaf$^{V600E}$ | 933 | >2700 | 6.8 |
| WM-266-4 | NRAS$^{Q61K}$ | 868 | >2700 | 4.5 |

EXAMPLE 3

Single agent and combinatorial effects on proliferation of inhibitors of RAF (Compound of Formula (I)) and PIK3Cα (Compound X) kinases in seven BRAF-mutant CRC-derived cell lines. All cell lines express the BRAFV600E protein. Cells harboring known or putative activating mutations in the PI3Kα gene are marked with a (*) and cells with PTEN loss marked with a (#). Cell proliferation was measured in 72 hr cell titer Glo™ assays and all results supplied are the result of at least triplicate measurements. Shown are single agent IC50 values for the Compound of Formula (I) and Compound X. Synergy score (SS) measurements as well as the combination index (CI50) at the 50% effect level are given for each combination) in Table 6. Interactions were deemed synergistic when SS values were ≥2.0 and CI values were ≤0.5. Interactions were deemed additive/synergistic when either SS values were ≥2.0 but CI values were >0.5 or SS values were <2.0 but CI values were ≤0.5. Interactions where termed additive when SS values were <2.0 and CI values were >0.5. Synergy calls are given in the "effect description" columns.

TABLE 6

Combinations of Cpd. Form (I) with Cpd X in BRAF$^{V600E}$ mutant CRC cell lines

| Cell Line Name | Cancer Type | Form (I) IC$_{50}$ [nM] | Cpd. X IC$_{50}$ [nM] | Combination SS | Combination CI$_{50}$ | Combination Effect Description |
|---|---|---|---|---|---|---|
| SW1417 | CRC | 235 | >2700 | 2.46 ± 0.06 | 0.27 ± 0.04 | Synergy |
| COLO 205 | CRC | 5.0 | >2700 | 3.80 ± 0.06 | 0.69 ± 0.01 | Additive/Synergy |
| LS411N | CRC | 18 | >2700 | 2.76 ± 0.07 | 0.49 ± 0.03 | Synergy |
| CL-34 | CRC | 30 | >2700 | 4.48 ± 0.1 | 0.57 ± 0.03 | Additive/Synergy |
| HT-29* | CRC | 49 | >2700 | 4.31 ± 0.06 | 0.21 ± 0.02 | Synergy |

TABLE 6-continued

Combinations of Cpd. Form (I) with Cpd X in BRAF$^{V600E}$ mutant CRC cell lines

| Cell Line Name | Cancer Type | Form (I) IC$_{50}$ [nM] | Cpd. X IC$_{50}$ [nM] | Combination SS | CI$_{50}$ | Effect Description |
|---|---|---|---|---|---|---|
| RKO* | CRC | 1965 | >2700 | 5.24 ± 0.05 | 0.22 ± 0.01 | Synergy |
| SNU-C5* | CRC | >2700 | >2700 | 2.44 ± 0.1 | 0.47 ± 0.07 | Synergy |
| OUMS-23# | CRC | >2700 | >2700 | 0.64 ± 0.06 | N/C | Additive |

EXAMPLE 4

Figure 2:
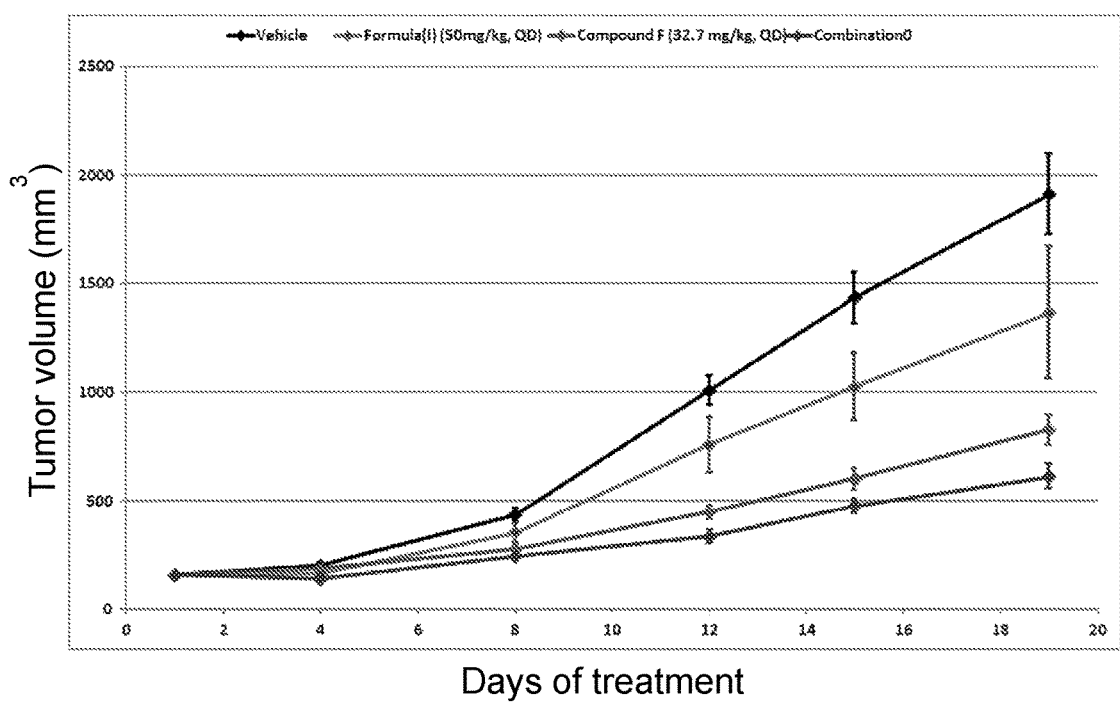
FIG. 2—shows the effect of the Compound of Formula (I) and Compound F as single agents and in combination on the growth of the RKO cell line model in vivo as described in Example 4.

This Example studies the effect of the Compound of Formula (I) and Compound F as single agents and in combination on the growth of the HT-29 and RKO cell line models in vivo. Concentration and dosing schedules for the inhibitors were 50 mg/kg q.d (Compound of Formula (I)), and 32.7 mg/kg q.d (Compound F). All compounds were dosed in combination as they were as single agents. Dosing was stopped at 28 days in the HT-29 model and after 21 days in the RKO model. The results are reported in FIGS. 1 and 2, respectively.

EXAMPLE 5

All cell lines were purchased from ATTC (SK-MEL-5, SK-MEL-24, UACC-62, COLO 741, COLO-800, WM-266-4, Colo205, LS411N, SW 1417), ECACC (MDST8), DSMZ (CL-34) and NCI (LOX IMVI). Cells were cultured either in RPMI1640 (ATCC, Catalog number 30-2001) or DMEM (ATCC, Catalog number 30-2002) supplemented with 10% (or 20% for CL-34 cells) FBS (GIBCO, Catalog number 10099-141) according to vendor recommendations. Cell lines were cultured in 37° C. and 5% CO2 incubator and expanded in T-75 flasks. In all cases cells were thawed from frozen stocks, expanded through ≥1 passage using 1:3 dilutions, counted and assessed for viability using a ViCell counter (Beckman-Coulter), prior to plating in 96-well or 6-well plates. To split and expand cell lines, cells were dislodged from flasks using 0.25% Trypsin-EDTA (GIBCO, Catalog number 25200). All cell lines were determined to be free of mycoplasma contamination as determined by a PCR detection methodology performed at Idexx Radii (Columbia, Mo., USA) and correctly identified by detection of a panel of SNPs.

The Compound of Formula (I) and Compound H dissolved in 100% DMSO (Cellgro, catalog number 25-290-CQC) at concentrations of 10 mM and stored at −200° C. until use. Compounds were arrayed in 2 ml deep 96-well plates (Greiner bio-one, catalog number 780271) serially diluted 3-fold seven times yielding concentration ranges from 22 nM to 16200 nM. Recombinant Human FGF basic was purchased from R&D system (Catalog number 233-FB), and reconstituted at 50 µg/ml in sterile PBS. It was used at a fixed concentration 100 ng/ml in all experiments.

For CellTiter-Glo™ assays, cells were dispensed into tissue culture treated 96-well plates (Costar, catalog number 3904) with a final volume of 80 µL of medium and at density of 3000 cells per well. 12 to 24 hrs after plating, 20 µL of each compound dilution series were transferred to plates containing the cells, resulting in compound concentration ranges of 2700 nM to 3.7 nM by 3-fold dilutions and a final DMSO concentration of 0.16%. The total volume in each well was 120 µL. Plates were incubated for 72 hrs and the effects of compounds on cell proliferation was determined using the CellTiter-Glo™ Luminescent Cell Viability Assay (CTG, Promega) and a Victor™ X4 plate reader (Perkin Elmer). For real-time growth assays cells were seeded into xCELLigence E-plates (Roche catalogue number 05232368001) at a density of 4000 cells per well in a total of 90 µl of media and 24 hrs after plating, 11 µl of media with or without compound was added to the wells. 2-4 replicate wells were plated for all cell lines and treatment groups with the exception of LGX818+FGF2 treated COLO 741 cells (N=1). Where indicated final concentrations of compounds and growth factor were 1 uM for Compound H, 100 ng/ml for FGF2, and either 100 nM (SK-MEL-5) or 500 nM (COLO 741) for the Compound of Formula (I). Cells were continuously monitored every two hours for seven days with the xCELLigence real-time impedance based cell analyzer. Impedance was measured using the electrodes on the E-plates, with increasing surface area coverage of cells creating greater electrode impedance. Electrode impedance was displayed as cell index values, and used as a proxy for cell viability and number. In all cases cell index values were normalized to a timepoint immediately following the addition of compound.

For Western analysis, cells were plated in 6-well (Costar, catalog number 3506) plates at a density of 5×105 cells per well in 2.0 ml of complete culture medium. Twelve to 24 hrs after plating, cells were treated with the various compounds, and in all experiments the Compound of Formula (I), Compound H, and FGF2 were used at final concentrations of 100 nM, 1.0 uM, and 100 ng/ml, respectively. Cells were harvested 2, and 24 hrs following the addition of compound in freshly prepared cell lysis buffer (Cell Signaling Technology Catalog number 9803); supplemented with both phosphatase (PhosStop, Roche Catalog number 04906845001) and protease inhibitors (Roche, catalog number 11697498001). Proteins from cell lysates were separated by electrophoresis though a NuPAGE 4-12% Bis-Tis midi gel (Novex, catalog number WG1402BX10), transferred to nitrocellulose membranes, which were subsequently incubated with antibodies from Cell Signaling Technology (Danvers, Mass., USA) recognizing p-AKT (S473, Catalog number 4058), total AKT (Catalog number 2920), p-ERK1/2 (T202/Y204, catalog number 9101), total ERK1/2 (catalog number 9107), p-MEK1/2 (S217/221, catalog number 9121) and β-actin (Ambion, catalog number AM4302). Western blots were visualized following incubation with IRDye 680RD Goat anti-Rabbit IgG (Li-Cor, Catalog number 926-68071) and IRDye 800 CW Goat anti-Mouse IgG (Li-Cor, Catalog number 926-32210) and scanning with an Odyssey Infrared Imager System (Li-Cor, Lincoln, Nebr., USA).

To determine whether FGFRs can rescue a subset of BRAFV600E mutant melanoma cell lines treated with the Compound of Formula (I), its anti-proliferative effects were examined in eleven T1799 mutant BRAF cell lines either in the presence or absence of the FGFR-activating ligand FGF2. In the absence of FGF2, IC50 values in six melanoma, and five CRC-derived cell lines ranged from 3.0 to 470 nM and 4.0 to 185 nM, respectively (Table 7). IC50 values measured for six of the cell lines were unaffected by the presence of FGF2, however, for the remaining five cell lines response to the Compound of Formula (I) was either greatly diminished (e.g. CL-34) or completely abolished (e.g. Is 411N). Thus, the presence of FGF2 is able to rescue a set of BRAFV600E melanoma-derived cell lines from the anti-proliferative effects of the B-Raf inhibitor of Formula (I). Furthermore, similar effects are also observed in BRAFV600E mutant cell lines derived from CRC tumors.

TABLE 7

| Cell Line Name | Cancer type | BRAF | PTEN | LGX818 $IC_{50}$[nM] | LGX818 + FGF2 $IC_{50}$[nM] |
|---|---|---|---|---|---|
| SK-MEL-5 | skin | mut | wt | 15 | >1000 |
| SK-MEL-24 | skin | mut | mut | 470 | 369 |
| UACC-62 | skin | mut | mut | 2.0 | 4 |
| COLO 741 | skin | mut | wt | 53 | 2652 |
| COLO-800 | skin | mut | wt | 9 | 12 |
| WM-266-4 | skin | mut** | mut | 3 | 4 |
| CL-34 | CRC | mut | wt | 38 | 730.0 |
| Colo 205 | CRC | mut | wt | 4 | 5 |
| LS411N | CRC | mut | wt | 185 | 9232 |
| MDST8 | CRC | mut* | unknown | 141 | 10000 |
| SW1417 | CRC | mut | wt | 165 | 364 |

Single agent IC50 values for the Compound of Formula (I) with or without 100 ng/ml FGF2 in a panel of BRAF T1799 mutant melanoma and CRC cell lines. Mutant (mut) and wildtype (wt) status was determined from published data. All BRAF mutations resulted in the V600E substitution, except in the cases of MDST8 (mut*) and WM-266-4 (mut**) which have V600K and V600D respectively. PTEN mut designations represent a summary call based on mutation, gene copy number, and mRNA expression information for the PTEN gene.

To determine whether rescue of BRAFV600E melanoma cell lines by FGF2 was dependent on FGFR signaling, we examined whether the selective FGFR inhibitor Compound H could prevent FGF2-mediated rescue. Two cell lines which were rescued to varying degrees by FGF2 (COLO 741, and SK-MEL-5, Table 8-1) were cultured in media containing the Compound of Formula (I) and FGF2 either in the presence or absence of Compound H and growth measured in real time.

Figure 3:
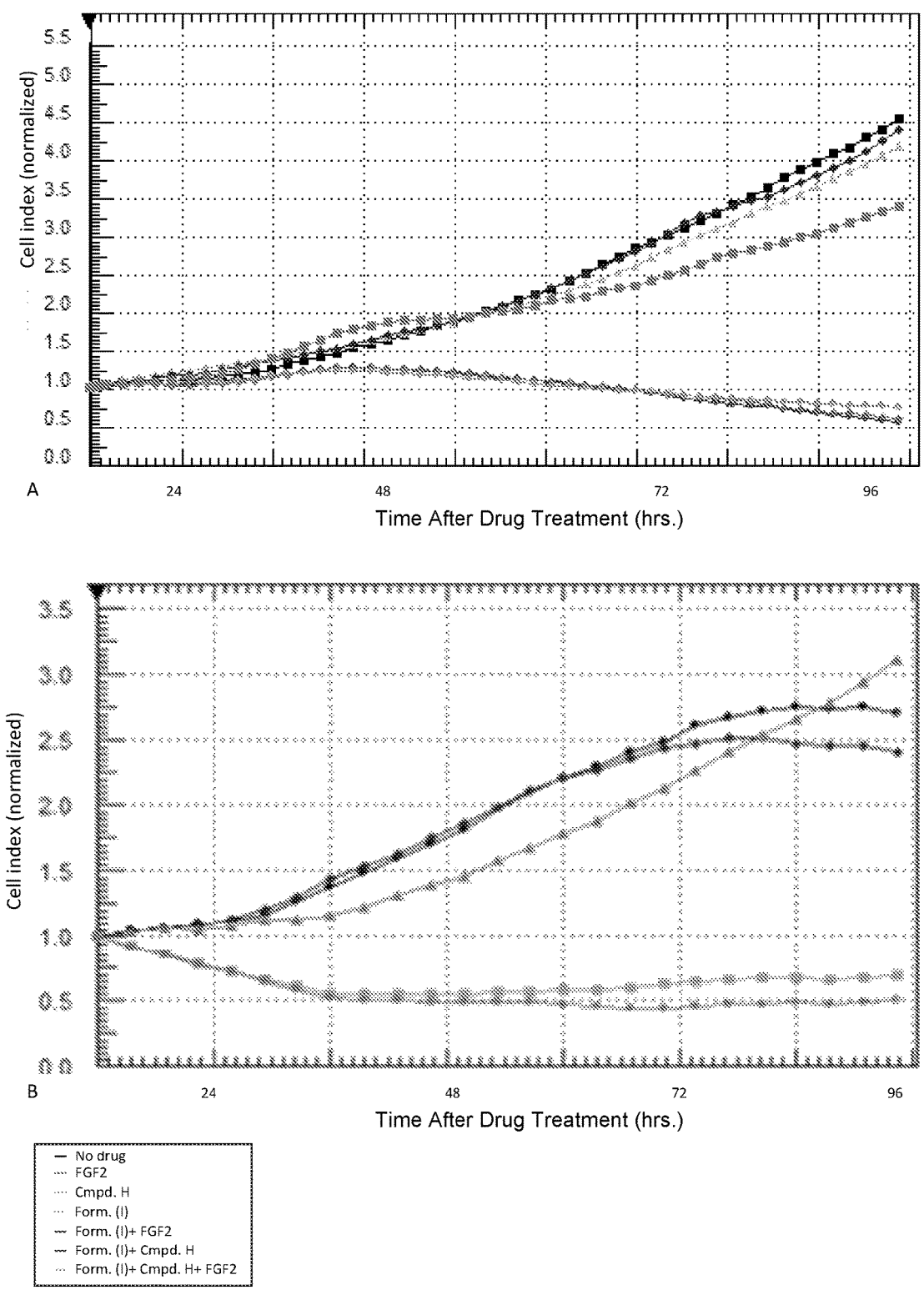
FIG. 3—shows the effect on proliferation of combining the RAF inhibitor (Compound of Formula I) with the FGFR inhibitor Compound H in two melanoma derived cell lines that harbor the BRAFV600E-encoding allele of BRAF. Shown is the growth in real time of the (Top A) COLO 741 and (Bottom B) SK-MEL-5 cell lines as measured using the xCELLigence impedance-based cell analyzer as discussed in Example 5. Where indicated FGF2 and Compound H were supplemented to the media at concentrations of 100 ng/ml, and 1 uM, respectively. The Compound of Formula (I) was used at 500 nM in (A) and 100 nM (B).

Consistent with the earlier IC50 data, the Compound of Formula (I) suppressed the growth of both cell lines, and this growth suppression was abrogated by the addition of FGF2 (FIG. 3). As a single agent Compound H did not affect the proliferation of either of the cell lines (panels A, not shown for SK-MEL-5), and when combined with the Compound of Formula (I) in the absence of FGF2 did not contribute to its single agent activity. When combined with the Compound of Formula (I) in the presence of FGF2, Compound H restored anti-proliferative effects to levels observed in the absence of FGF2. These results indicate that FGF2 mediated rescue can be prevented via the addition of the selective FGFR inhibitor Compound H.

Figure 4:
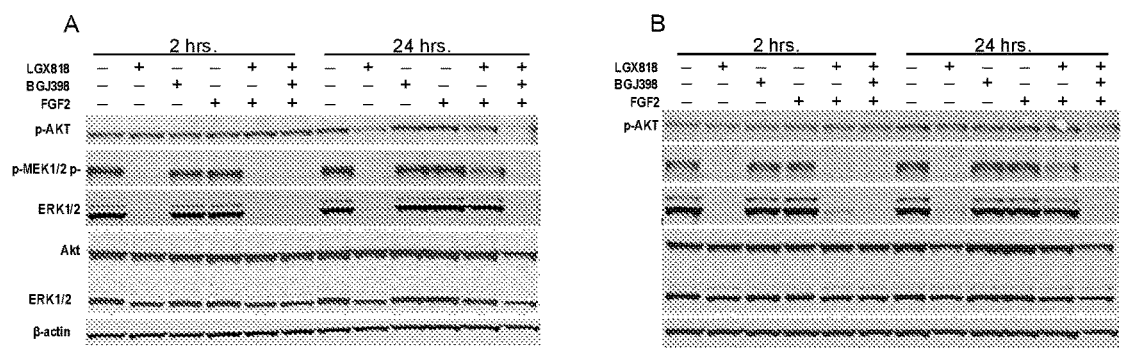
FIG. 4—The effect on signaling of combining the Compound of Formula (I) with the FGFR inhibitor Compound H and the FGFR ligand FGF2 in two BRAFV600E mutant melanoma-derived cell lines in vitro. Shown is western analysis of both phosphorylated and total AKT, ERK1/2, and MEK1/2 proteins isolated from (A) COLO 74 and (B) SK-MEL-5 cells following treatment with the Compound of Formula (I) (100 nM), FGF2 (100 ng/ml), and Compound H (1 uM). Cells were treated for 2 and 24 hours with agents singly and in combination as discussed in Example 5.

To investigate whether either restored MAPK or activated PIK3C signaling might underlie FGF2-mediated rescue the effects of FGF2 on MAPK and PIK3C signaling were examined via western-blot analysis of phosphorylated MEK1/2 (MAP2K1/2), ERK1/2 (MAPK1/2) and AKT1/2/3. As demonstrated in FIG. 4, incubation of COLO 741 and SK-MEL-5 cells with the Compound of Formula (I) resulted in marked suppression of MAPK signaling at both 2 and 24 hours following compound addition as judged by reductions in levels of both phosphorylated MEK and ERK. Phosphorylated levels of AKT were unaffected at 2 hours, but showed modest decreases at 24 hrs in COLO 741 cells. In contrast, neither FGF2 nor Compound H when added as single agents affected signaling at either 2 or 24 hours. When FGF2 and the Compound of Formula (I) were combined, minimal changes in signaling relative to the Compound of Formula (I) alone were observed two hours after treatment (although slight increases in p-ERK were observed in SK-MEL-5 cells), however, levels of both phosphorylated MEK and ERK had been largely, although not completely, restored by 24 hrs. Lastly, the addition Compound H to the Compound of Formula (I)/FGF2 combination completely abolished the FGF2-induced changes in MAPK and PIK3C signaling. These data strongly suggest the suppression of the B-Raf inhibitor's anti-proliferative effects by FGF2 results from a re-activation of MAPK signaling, and indicate that Compound H is able to completely suppress these FGF2 induced signaling changes.

EXAMPLE 6

Objective: To evaluate the efficacy of the combination of the Compound of Formula (I) and the CDK 4 inhibitor Compound C in the HMEX1906 primary melanoma model that is grown in the presence of and is resistant to 5 mg/kg the Compound of Formula (I) (HMEX1906-R5)

Drug formulation: Compound C is formulated in 0.5% MC/0.5% Tween80 and the Compound of Formula (I) is formulated in 20% PEG300/3% ETPGS.

Tumors are chopped/minced into cell line like suspension (tumors homogenized). 7 mL of matrigel added and 1.5 mL of HBSS. Suspension warmed in palm until Matrigel is thick and implanted with a 18G needle s.c right flank of female nude mice.

The mice were assigned to the following groups at 18 days post implant with an average tumor volume of 266 mm³ and average body weight of 25 grams.

Groups: 10 mice/group, route PO, dose volume 0.2 mL

Group 1: Vehicle, 0 mg/kg bid×14

Group 2: Compound C, 250 mg/kg qd×21

Group 3: Compound of Formula (I), 5 mg/kg bid×21

Group 4: Compound C 250 mg/kg qd×21+Compound of Formula (I) 5 mg/kg bid×21

Results:

| Group | Mean change of tumor volume vs control (T/C) (%) | Regression (%) | Mean change of tumor volume (mm3 ± SEM) | Mean change of body weight (% ± SEM) | Survival (Survivors/Total) |
|---|---|---|---|---|---|
| 1 | 100 | — | 2092 ± 154 | 4.2 ± 2.6 | 7/10* |
| 2 | 4 | — | 86 ± 26 | 5.3 ± 1.4 | 10/10 |
| 3 | 39 | — | 807 ± 106 | 3.5 ± 1.1 | 10/10 |
| 4 | — | 64.32 | −170 ± 45 | 7.1 ± 1.6 | 10/10 |

*3 mice were euthanized due to large tumor

The invention claimed is:

1. A therapeutic combination consisting essentially of a B-Raf inhibitor of Formula (I)

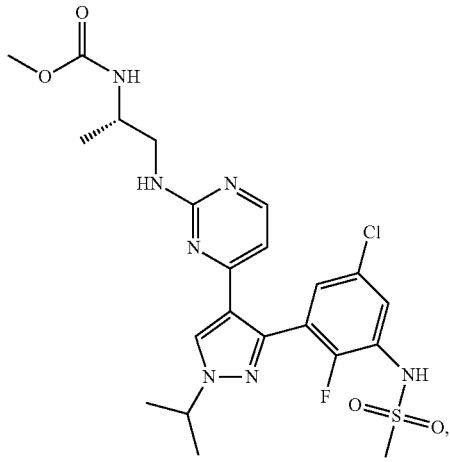

(I)

or a pharmaceutically acceptable salt thereof; and a second inhibitor which is a PI3 kinase inhibitor of 5-(2,6-di-morpholin-4-yl-pyrimidin-4-yl)-4-trifluoromethyl-pyridin-2-ylamine (Compound F) or (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (Compound X), or a pharmaceutically acceptable salt thereof, for separate, simultaneous or sequential administration.

2. The therapeutic combination of claim 1, wherein the PI3 kinase inhibitor is 5-(2,6-di-morpholin-4-yl-pyrimidin-4-yl)-4-trifluoromethyl-pyridin-2-ylamine (Compound F), or a pharmaceutically acceptable salt thereof.

3. The therapeutic combination of claim 1, wherein the PI3 kinase inhibitor is (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (Compound X), or a pharmaceutically acceptable salt thereof.

* * * * *